(12) United States Patent     (10) Patent No.: US 7,812,324 B2
Connally et al.     (45) Date of Patent: Oct. 12, 2010

(54) FLUORESCENCE DETECTION

(75) Inventors: Russell Connally, Marsfield (AU);
James Austin Piper, Huntley's Cove (AU)

(73) Assignee: Macquarie University, New South Wales (AU)

( * ) Notice: Subject to any disclaimer, the term of this patent is extended or adjusted under 35 U.S.C. 154(b) by 329 days.

(21) Appl. No.: 11/577,216

(22) PCT Filed: Oct. 17, 2005

(86) PCT No.: PCT/AU2005/001606

§ 371 (c)(1),
(2), (4) Date: Jun. 4, 2008

(87) PCT Pub. No.: WO2006/089342

PCT Pub. Date: Aug. 31, 2006

(65) Prior Publication Data

US 2008/0265177 A1    Oct. 30, 2008

(51) Int. Cl.
*C12M 1/34* (2006.01)
*G01N 21/64* (2006.01)

(52) U.S. Cl. ............... 250/461.2; 250/461.1; 250/484.2; 435/287.2

(58) Field of Classification Search ............... 250/461.1, 250/461.2, 484.2; 435/287.2
See application file for complete search history.

(56) References Cited

U.S. PATENT DOCUMENTS

| 6,200,752 | B1 | 3/2001 | Lakowicz | |
| 2004/0015062 | A1 | 1/2004 | Ntziachristos | ............... 600/312 |
| 2004/0043502 | A1 | 3/2004 | Song | ............... 436/172 |
| 2005/0221351 | A1 | 10/2005 | Ryu | ............... 435/6 |

FOREIGN PATENT DOCUMENTS

| DE | 10259677 | 7/2004 | |
| WO | WO 01/009605 A1 | 2/2001 | ............... 33/48 |

OTHER PUBLICATIONS

Coates et al. (2003). "Back-illuminated Electron Multiplying Technology: The World's Most Sensitive CCD for Ultra Low-Light Microscopy." Proc. SPIE (4962): p. 319-328.*

(Continued)

*Primary Examiner*—David P Porta
*Assistant Examiner*—Casey Bryant
(74) *Attorney, Agent, or Firm*—Paul Davis; Goodwin Procter LLP

(57) ABSTRACT

A fluorescence detection system comprises a light source (22), dichroic mirror (32), excitation port (16), emission port (14), and a detector. The light source (22) is, for example, a pulsed ultraviolet LED, with a light emission that decays sufficiently rapidly to permit gated detection of fluorescence from a fluorescently-labelled species, at a time when it is distinguishable from autofluorescence. The detector is, for example, an electron multiplying CCD, with high gain on-chip amplification. A circuit (26) may be used to control a repeating cycle of (i) generation of a 20-200 microsecond UV. pulse; (ii) a gate delay of 1-5 microseconds; and (iii) a 10-800 microsecond detection period. This allows time-resolved-fluorescence-microscopy with real time or near real time operation.

68 Claims, 7 Drawing Sheets

OTHER PUBLICATIONS

Connally et al. (2003). "Novel Flashlamp Based Time-Resolved Fluorescence Microscope Reduces Autofluorescence for 30-Fold Contrast Enhancement in Environmental Samples." Proc. SPIE (4964): 14-23.*

CoolView Low Light Camera (http://www.photonic-science.co.uk/zz_CoolView_EM.html).

Denvir J. Donal et al., (http://www.emccd.com/Electron_Multiplying_CCD_Technology-Application_To_Ultrasensitive_Detection_Of_Biomolecules.pdf).

European Extended Supplementary Search Report for Application No. EP 05857291.8.

Colin G. Coates et al: Ultra Sensitivity, Speed and Resolution: Optimizing Low-Light Microscopy with the Back-Illuminated Electron Multiplying CCD; Proceedings of the SPIE-The International Society For Optical Engineering vol. 5139, No. 1 Jan. 1, 2003 pp. 56-66; XP002365051.

* cited by examiner

FLUORESCENCE DETECTION

TECHNICAL FIELD

The present invention relates to fluorescence detection systems, particularly time resolved fluorescence detection systems.

BACKGROUND OF THE INVENTION

Various types of immunoassay involve attaching fluorescent labels either directly or indirectly to a species of interest, for example a microorganism. Animal, plant and microbial cells contain significant amounts of aromatic compounds, many of which are intrinsically fluorescent (autofluorescent) when excited at an appropriate wavelength. The range of fluorescent substances of biological origin described in the biochemical literature is large and includes chlorophyll, haemoglobin and protein. When these autofluorescent materials have high quantum yields (typically >0.02) they can present a problem of spurious fluorescence against which fluorescent labels of interest must be detected.

Autofluorescence can occur throughout the visible spectrum and is typically a short-lived phenomena with a lifetime ($\tau$) measured in nanoseconds. Autofluorophores may have a fluorescence lifetime ($\tau$) ranging from 1 to 100 nanoseconds and synthetic fluorophores are available with $\tau$ more than 20,000 times longer (millisecond lifetimes).

A number of methods have been applied to reduce the severity of the problem of autofluorescence and time-resolved fluorescence microscopy (TRFM) is a proven technique that can largely eliminate its effects. Time-resolved fluorescence microscopes can roughly be divided into two types: those designed to discriminate fluorophores with very short lifetimes (nanoseconds) operating in the frequency domain, and instruments that exploit the time domain and employ fluorophores with longer fluorescence lifetimes (microseconds and greater). Time-resolved fluorescence techniques have been developed to exploit the (comparatively) long fluorescence lifetimes (>300 $\mu$s) observed with lanthanide chelates. Europium and terbium chelates are often employed in fluorescent labels due to their useful visible emission (red and green respectively), however the antenna molecule used to transfer energy to the chelated lanthanide ion typically requires excitation in the UV range (320 to 360 nm). Time-resolved fluorescence methods employ pulsed-excitation of the fluorophore, followed by a gate-delay phase to permit decay of short-lived fluorescence. A disadvantage with the use of flashlamps as the excitation source is that the duration of the gate-delay period must be extended to ensure that light from the decaying arc plasma has decayed to zero. Flashlamp plasma can persist for hundreds of microseconds even for lamps with rated arc duration of 1 or 2 $\mu$s and the faint emission from the plasma can obscure the weak emission from most fluorophores for a significant time.

Detection of rare organisms that may occur in the early stages of infection or in cases where the organisms are generally unculturable is very difficult when even moderate autofluorescence is present. Suppression of background autofluorescence results in much greater detection success and consequently fluorescence microscopy techniques may be applied in circumstances where they are currently not used due to the presence of autofluorophores.

No current techniques eliminate the problem of autofluorescence under all circumstances, however the use of narrow passband filters is the most common and readily available technique. In this manner a specific narrow excitation spectrum is used to excite fluorescence from the probe with minimal competing fluorescence from autofluorophores. The emission spectrum is also selectively captured within a narrow passband to limit the impact of autofluorescence. The method relies on the availability of suitable fluorophores with spectral characteristics sufficiently different from the principal interfering autofluorophore.

Conventional methods of generating a pulsed excitation source for time-resolved fluorescence detection have often relied on the use of mechanical shutters (chopper wheel). Although systems employing this techniques have the advantage of suppressing autofluorescence in real-time, they are not ideal. They have disadvantages of low pulse repetition speed, slow rise and fall-time of the excitation pulse, sensitivity to vibration due to the very rapid rotation of the chopper wheel and uneven illumination across the viewing plane (sunrise-sunset effect). Mechanical systems are also generally found to be less reliable than electronic systems. A second method of blocking light from the excitation source is based on ferro-electric liquid crystals that act to shift the plane of polarization of light reaching the observer. The liquid crystal is sandwiched between two polarizing elements that are oriented to block the passage of any light unless it is rotated into the plane of the analyser. The optical shutter is controlled by applying a voltage to the ferro-electric liquid crystal so that the plane of polarization is rotated in the correct orientation to pass through the exit analyser. A disadvantage of ferro-electric liquid crystal shutters is the relatively slow operation of the shutter, with a period of 80 microseconds required before the shutter has opened or closed to 90% of maximum.

UV excitation energy should ideally be delivered with very rapid (sub-microsecond) rise and fall times for maximum efficiency of an instrument. Solid-state sources are easily switched at low voltages with nanosecond accuracy, however until recently no devices were available that operate in the required region of the near UV spectrum, for example in the range of 330-370 nm. Prior to the appearance of solid-state UV sources on the market, a number of sub-optimal methods of generating pulsed UV were employed. These included mechanical choppers interrupting a UV rich light source, acousto-optical switches to deflect laser UV sources and rapid discharge flashlamps (as in our prototype instrument).

Detection of the faint fluorescence from the time-resolved fluorescence probe typically required a cooled CCD camera integrating a faint signal over a period of minutes, or the use of an image intensified, time-gated CCD camera. The latter instrument has the advantage of speed, however resolution is inferior to the cooled CCD camera and the cost is a significant factor in the final expense of a TRFM system.

There is therefore a need for a fluorescence detection system with fast switching speeds, preferably in the nanosecond timescale. There is a further need for a fluorescence detection system with improved sensitivity, so that infrequent fluorescence events may be detected. The systems would preferably be relatively inexpensive.

OBJECT OF THE INVENTION

It is an object of the present invention to overcome or substantially ameliorate at least one of the above disadvantages. It is a further object to at least partly satisfy at least one of the above needs.

SUMMARY OF THE INVENTION

In a broad form of the invention there is provided a fluorescence detection system comprising:

a light source for generating a light emission to excite fluorescence in a fluorescently labeled species in a sample, and a detector for detecting the fluorescence, wherein either decay of the light emission from the light source is such as to permit measurement of the fluorescence at a time at which the fluorescence is distinguishable from the autofluorescence or the detector is an on-chip amplified charge coupled device (CCD) for detecting the fluorescence, or both.

In a first aspect of the invention there is provided a fluorescence detection system comprising:

a light source for generating a light emission to excite fluorescence in a fluorescently labeled species in a sample, and a detector for detecting the fluorescence, wherein decay of the light emission from the light source is such (e.g. sufficiently rapid) so as to permit measurement of the fluorescence at a time at which the fluorescence is distinguishable from the autofluorescence.

The light emission may be a light pulse whose decay is sufficiently rapid so as to enable measurement of the fluorescence at a time at which the fluorescence is distinguishable from the autofluorescence. The light source may be such that, at a time after decay of the light emission, or of the autofluorescence, or of both, the fluorescence has not decayed substantially. At the time after decay of the light emission, or of the autofluorescence, the fluorescence may have decayed by less than about 50% of its maximum intensity, or less than about 40, 30, 25, 20, 15, 10, 5, 4, 3, 2, 1, 0.5 or 0.1% of its maximum intensity. The time may be sufficient for the light emission and/or the autofluorescence to decay to less than about 15% of its/their original intensity, or less than about 10, 9, 8, 7, 6, 5, 4, 3, 2, 1, 0.5, 0.1, 0.05 or 0.01% of its/their original intensity. At the time after decay of the light emission, or of the autofluorescence, the ratio between the maximum intensity of the fluorescence and the maximum intensity of the autofluorescence may be greater than about 1.5 to 1, or greater than about 2, 3, 4, 5, 6, 7, 8, 9, 10, 15, 20, 30, 40, 50, 100, 150, 200, 300, 400, 500, 1000, 1500, 2000, 2500, 3000, 3500, 4000, 4500 or 5000 to 1. The ratio may be between about 1.5 and 5000 to 1, or about 1.5 and 1000 or about 1.5 and 500 or about 1.5 and 100 or about 1.5 and 50 or about 10 and 5000 or about 100 and 5000 or about 100 and 5000 or about 1000 and 5000 or about 10 and 2000 or about 100 and 1000 to 1, and may be about 1.5, 2, 3, 4, 5, 6, 7, 8, 9, 10, 15, 20, 30, 40, 50, 60, 70, 80, 90, 100, 150, 200, 300, 400, 500, 1000, 1500, 2000, 2500, 3000, 3500, 4000, 4500 or 5000 to 1. The time may be less than about 10 microseconds, or less than about 9, 8, 7, 6, 5, 4, 3, 2 or 1 microsecond. It may be between about 50 ns and 10 microseconds, or between about 50 ns and 1 microsecond or between about 50 and 500 or about 50 and 200 ns or about 500 ns and 5 microseconds or about 1 and 10 or about 1 and 5 or about 1 and 2 microseconds, and may be about 50, 100, 200, 300, 400, 500, 600, 700, 800 or 900 ns or about 1, 2, 3, 4, 5, 6, 7, 8, 9 or 10 microseconds.

The light source may be a solid state light source, and may be a light emitting diode (LED). The light source may be a gallium nitride (GaN) based or indium gallium nitride (InGaN) based LED. The light source may be capable of producing a light emission in the ultraviolet wavelength range, for example in the range between about 275 nm and about 395 nm, and may be capable of producing a light emission of a wavelength that is capable of being absorbed by a fluorescent marker molecule or a species labeled with a fluorescent label. The light source may be capable of producing pulsed light emission. The duration of pulses of the pulsed light emission may be between about 10 ns and about 200 microseconds, and the time between successive pulses may be between about 1 microsecond and about 1 ms. The light source may have optical output power of between about 2 and 100 mW. The fluorescence detection system may be a time resolved fluorescence detection system. The fluorescence detection system may comprise a microscope, and may be a fluorescence detection microscope or a time resolved fluorescence detection microscope (TRFM). The fluorescence detection system may have at least one detector for detecting fluorescence from the sample, and may have an eyepiece to enable an operator to observe the sample, and may have a switching device to switch between the detector and the eyepiece, and/or to switch between different types of detector. The time resolved detection system may have a controller for imparting a gate-delay (ie a time between the end of a light pulse from the light source and the commencement of detection by the detector), and the gate delay may be precisely controlled. The gate delay may be less than about 10 microseconds. The system may also have a computer for acquiring, storing and/or presenting data from the detector. The system may not have a shutter for preventing the light emission from being detected by the detector.

In an embodiment, there is provided a fluorescence detection system comprising a light source for generating a light emission to excite fluorescence in a sample and a detector for detecting the fluorescence, wherein the light emission decays within about 10 microseconds, or within about 1 microsecond.

In another embodiment the fluorescence detection system comprises:

a light source for generating a light emission to excite fluorescence in a sample, wherein the light emission decays within about 10 microseconds, or within about 1 microsecond;

a dichroic mirror for directing the light emission from the light source towards the sample;

a detector for detecting the fluorescence from the sample;

optionally an eyepiece to enable an operator to observe the sample;

optionally a switching device to switch between the detector and the eyepiece; and an emission port for transmitting the fluorescence from the sample to the detector or eyepiece.

In yet another embodiment there is provided a time resolved fluorescence microscope comprising:

a light source for generating a light emission to excite fluorescence in a sample, wherein the light emission decays within about 10 microseconds, or within about 1 microsecond, and said light source being capable of producing pulsed light emission having pulses of between about 10 ns and about 200 microseconds and a time between successive pulses of between about 10 microseconds and about 10 ms;

a dichroic mirror for directing the light emission from the light source towards the sample;

an objective lens for magnifying the fluorescence from the sample;

a detector for detecting the fluorescence from the sample, a controller for imparting a gate-delay of less than about 10 microseconds; and an emission port for transmitting the fluorescence from the sample to the detector.

In a second aspect of the invention there is provided a fluorescence detection system comprising a light source for generating a light emission to excite fluorescence in a sample and an on-chip amplified charge coupled device (CCD) for detecting the fluorescence.

The CCD may be capable of on-chip amplification of greater than 30, and may be a high gain CCD. The fluorescence detection system may be a time resolved fluorescence detection system. The fluorescence detection system may comprise a microscope, and may be a fluorescence detection microscope or a time resolved fluorescence detection microscope. The system may also comprise an integrator for off-chip integration. The integrator may be a computer or a data processor or a field programmable gate array, or some other suitable integrator.

In an embodiment the fluorescence detection system comprises:
  a light source for generating a light emission to excite fluorescence in a sample;
  a dichroic mirror for directing the light emission from the light source towards the sample;
  a high gain on-chip amplified CCD detector, for detecting the fluorescence from the sample; and
  an emission port for transmitting the fluorescence from the sample to the detector.

In another embodiment there is provided a time resolved fluorescence microscope comprising:
  a pulsed light source for generating a light emission to excite fluorescence in a sample;
  a dichroic mirror for directing the light emission from the light source towards the sample;
  an objective lens for magnifying the fluorescence from the sample;
  a high gain on-chip amplified CCD detector for detecting the fluorescence from the sample;
  an off-chip integrator for integrating signals from the detector;
  a controller for imparting a gate-delay of less than about 10 microseconds; and
  an emission port for transmitting the fluorescence from the sample to the detector.

In a third aspect of the invention there is provided a fluorescence detection system comprising:
  a light source for generating a light emission to excite fluorescence in a fluorescently labeled species in a sample, and
  a high gain on-chip amplified charge coupled device (CCD) for detecting the fluorescence from the sample, wherein the light source is such that decay of the light emission is sufficiently rapid to enable measurement of the fluorescence at a time at which the fluorescence is distinguishable from the autofluorescence. The light source may be such that, at a time after decay of the light emission, or of the autofluorescence, or of both, the fluorescence has not decayed substantially.

At the time after decay of the light emission, or of the autofluorescence, the fluorescence may have decayed by less than about 50% of its maximum intensity, or less than about 40, 30, 25, 20, 15, 10, 5, 2, 1, 0.5 or 0.1% of its maximum intensity. The time may be sufficient for the light emission and/or the autofluorescence to decay to less than about 15% of its/their original intensity, or less than about 10, 5, 4, 3, 2, 1, 0.5, 0.1, 0.05 or 0.01% or its/their original intensity. The time may be less than about 10 microseconds, or less than about 9, 8, 7, 6, 5, 4, 3, 2 or 1 microsecond. It may be between about 50 ns and 10 microseconds, or between about 50 ns and 1 microsecond or between about 50 and 500 or about 50 and 200 ns or about 500 ns and 5 microseconds or about 1 and 10 microseconds or about 1 and 5 or about 1 and 2 microseconds, and may be about 50, 100, 200, 300, 400, 500, 600, 700, 800 or 900 ns or about 1, 2, 3, 4, 5, 6, 7, 8, 9 or 10 microseconds.

The light source may be a solid state light source, and may be a light emitting diode (LED). The light source may be a gallium nitride (GaN) or indium gallium nitride (InGaN) based LED. The light source may be capable of producing a light emission in the ultraviolet wavelength range, for example in the range between about 275 nm and about 395 nm, and may be capable of producing a light emission of a wavelength that is capable of being absorbed by a fluorescent marker molecule. The light source may be capable of producing pulsed light emission. The duration of pulses of the pulsed light emission may be between about 10 ns and about 200 microseconds, and the time between successive pulses may be between about 10 microsecond and about 10 ms. The LED light source may have an optical output power of between about 2 and 100 mW. High output power of 100 mW being the preferred excitation source.

The CCD may be capable of on-chip amplification of greater than 30, and may be a high gain CCD. The fluorescence detection system may be a time resolved fluorescence detection system. The system may have a controller for imparting a gate-delay of less than about 10 microseconds. The fluorescence detection system may comprise a microscope, and may be a fluorescence detection microscope or a time resolved fluorescence detection microscope. The system may also comprise an integrator for off-chip integration. The integrator may be a computer or a data processor or a field programmable gate array, or some other suitable integrator.

In an embodiment there is provided a fluorescence detection system comprising:
  a light source for generating a light emission to excite fluorescence in a sample, wherein the light emission decays within about 1 microsecond; and
  a high gain on-chip amplified charge coupled device (CCD) for detecting the fluorescence from the sample.

In another embodiment the fluorescence detection system comprises:
  a light source for generating a light emission to excite fluorescence in a sample, wherein the light emission decays within about 1 microsecond;
  a dichroic mirror for directing the light emission from the light source towards the sample;
  a high gain on-chip amplified charge coupled device (CCD) for detecting the fluorescence from the sample
  an off-chip integrator for integrating signals from the detector;
  a controller for imparting a gate-delay of less than about 10 microseconds; and
  an emission port for transmitting the fluorescence from the sample to the CCD.

In a fourth aspect of the invention, there is provided a time resolved fluorescence microscope comprising:
  a light source for generating a light emission to excite fluorescence in a fluorescently labeled species in a sample;
  a dichroic mirror for directing the light emission from the light source towards the sample;
  an objective lens for magnifying the fluorescence from the sample;
  a high gain on-chip amplified charge coupled device (CCD) for detecting the fluorescence from the sample;
  a controller for imparting a gate-delay of less than about 10 microseconds; and
  an emission port for transmitting the fluorescence from the sample to the CCD;

wherein the light source is such that decay of the light emission is sufficiently rapid to enable measurement of the fluorescence at a time at which the fluorescence is distinguishable from the autofluorescence. The light source may be such that, at a time after decay of the light emission, or of the autofluorescence, or of both, the fluorescence has not decayed substantially. The light source may have optical output power of between about 2 and 100 mW. The microscope may also comprise an integrator for off-chip integration. The integrator may be a computer or a data processor or a field programmable gate array, or some other suitable integrator.

In an embodiment there is provided a time resolved fluorescence microscope comprising:
- a light source for generating a light emission to excite fluorescence in a sample, wherein the light emission decays within about 10 microseconds, or within about 1 microsecond, and said light source being capable of producing pulsed light emission having pulses of between about 10 ns and about 200 microseconds and a time between successive pulses of between about 1 microsecond and about 10 ms;
- a dichroic mirror for directing the light emission from the light source towards the sample;
- an objective lens for magnifying the fluorescence from the sample;
- a high gain on-chip amplified charge coupled device (CCD) for detecting the fluorescence from the sample after it has been magnified;
- an off-chip integrator for integrating signals from the detector;
- a controller for imparting a gate-delay of less than about 10 microseconds; and
- an emission port for transmitting the fluorescence from the sample to the CCD.

In a fifth aspect of the invention there is provided a method for detecting and/or counting species in a sample, said species having been labelled with a fluorophore, said method comprising:
- placing the sample in a fluorescence detection system according to the present invention or a time resolved fluorescence microscope according to the present invention;
- exposing the sample to light from the light source;
- detecting fluorescence from the sample using the detector; and
- optionally determining a number of fluorescent entities in the sample.

The step of exposing may comprise exposing the sample to light from a pulsed light source, and the step of detecting may comprise the steps of:
- waiting for a predetermined period after the end of a pulse from the light source;
- detecting fluorescence after the predetermined period; and
- stopping the detecting before commencement of the subsequent pulse from the light source.

The predetermined period (the gate-delay) may be less than about 10 microseconds. The method may also comprise magnifying the fluorescence from the sample before detecting it.

In a sixth aspect of the invention there is provided a kit for modifying a fluorescence microscope comprising one or more components selected from:
- a light source for generating a light emission to excite fluorescence in a fluorescently labeled species in a sample; and
- a high gain on-chip amplified charge coupled device (CCD) for detecting the fluorescence from the sample;

wherein the light source is such that decay of the light emission is sufficiently rapid to enable measurement of the fluorescence at a time at which the fluorescence is distinguishable from the autofluorescence. The light source may be such that, at a time after decay of the light emission, or of the autofluorescence, or of both, the fluorescence has not decayed substantially.

The light source may be such that the light emission decays within about 1 microsecond. At the time after decay of a pulse of the light emission, or of the autofluorescence, the fluorescence may have decayed by less than 50% of its maximum intensity, or less than 40, 30, 25, 20, 25, 10, 5, 2, 1, 0.5 or 0.1% of its maximum intensity. The time may be sufficient for the pulse and/or the autofluorescence to decay to less than about 15% of its/their original intensity, or less than about 10, 5, 4, 3, 2, 1, 0.5, 0.1, 0.05 or 0.01% or its/their original intensity. The time may be less than about 10 microseconds, or less than about 9, 8, 7, 6, 5, 4, 3, 2 or 1 microsecond. It may be between about 50 ns and 10 microseconds, or between about 50 ns and 1 microsecond or between about 50 and 500 or about 50 and 200 ns or about 500 ns and 5 microseconds or about 1 and 10 or about 1 and 5 or about 1 and 2 microseconds, and may be about 50, 100, 200, 300, 400, 500, 600, 700, 800 or 900 ns or about 1, 2, 3, 4, 5, 6, 7, 8, 9 or 10 microseconds. The light source may be capable of producing pulsed light emission having pulses of between about 10 ns and about 200 microseconds and a time between successive pulses of between about 10 microseconds and about 10 ms. The light source may have optical output power of between about 2 and 100 mW.

The kit may additionally comprise one or more of:
- a controller for controlling the light source, for example for controlling pulsing of the light source. The controller may be a printed circuit board, a computer, a microprocessor, a chip, a microchip or some other controller. It may also control the CCD. It may be capable of imparting a gate-delay of less than about 10 microseconds;
- a collimator, for example a collimating lens;
- a dichroic mirror, which may be reflective, partially reflective or highly reflective towards the light emission, and may be transmissive, partially transmissive or highly transmissive towards the fluorescence;
- a first light transmitter for transmitting the light emission towards a sample. The first light transmitter may also serve to transmit the fluorescence from the sample towards the dichroic mirror. The first light transmitter may be a window, a port, for example an excitation port or some other transmitter. It may be transmissive, partially transmissive or highly transmissive towards the light emission, and may also be transmissive, partially transmissive or highly transmissive towards the fluorescence;
- a second light transmitter for transmitting the fluorescence towards a detector and/or an eyepiece. The second light transmitter may be a window, a port, for example an emission port or some other transmitter. It may be transmissive, partially transmissive or highly transmissive towards the fluorescence; and
- a housing, such as a filter-box housing, for housing any one or more of the above.

In an embodiment the kit comprises:
- a light source for generating a light emission to excite fluorescence in a sample, wherein the light emission decays within about 10 microseconds, or within about 1 microsecond;
- a dichroic mirror for directing the light emission from the light source towards the sample;

a high gain on-chip amplified charge coupled device (CCD) for detecting the fluorescence from the sample; and an emission port for transmitting the fluorescence from the sample to the CCD.

In another embodiment the kit comprises:

a light source for generating a pulsed light emission to excite fluorescence in a sample, wherein the light emission decays within about 10 microseconds, or within about 1 microsecond;

a controller for controlling pulsing of the light source and for imparting a gate-delay of less than about 10 microseconds;

a collimator for collimating the light emission;

a dichroic mirror for directing the light emission towards the sample;

a first light transmitter for transmitting the light emission towards the sample, and for transmitting the fluorescence from the sample towards the dichroic mirror;

a high gain on-chip amplified charge coupled device (CCD) for detecting the fluorescence from the sample; and a second light transmitter for transmitting the fluorescence towards the CCD.

In a seventh aspect of the invention there is provided a method for modifying a fluorescence microscope comprising fitting a kit according to the invention to said microscope. The method may comprise fitting to said microscope one or more components selected from:

a light source for generating a light emission to excite fluorescence in a fluorescently labeled species in a sample; and a high gain on-chip amplified charge coupled device (CCD) for detecting the fluorescence from the sample;

wherein the light source is such that decay of the light emission is sufficiently rapid to enable measurement of the fluorescence at a time at which the fluorescence is distinguishable from the autofluorescence.

The invention also provides a fluorescence microscope comprising a kit according to the invention and additionally provides a fluorescence microscope modified according to the method of the seventh aspect of the invention.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENTS

Figure 1:
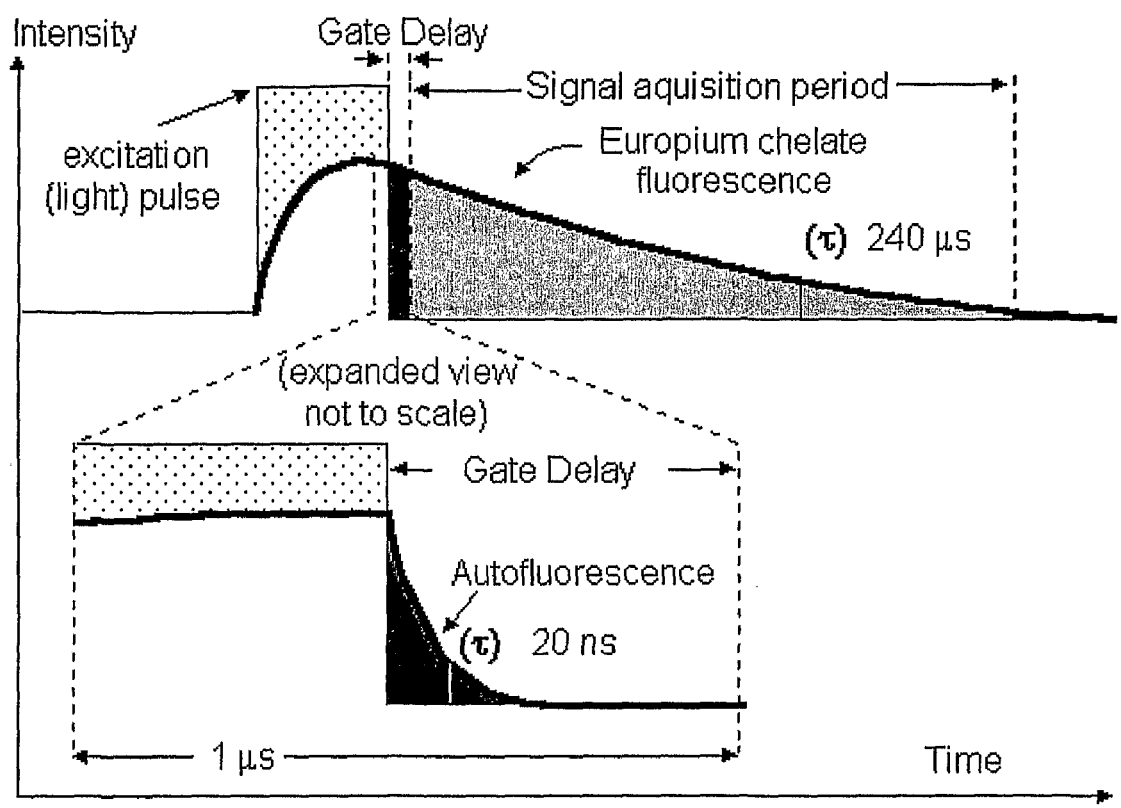
FIG. 1 is a graph showing light intensity over time during an excitation pulse and subsequent fluorescence decay.

The invention disclosed herein relates, in certain embodiments, to an improved design of a fluorescence detection system such as a time-resolved fluorescence microscope (TRFM) that operates in the time domain and employs fluorescent dyes with a fluorescence lifetime, $\tau$, greater than 200 microseconds. In order to discriminate between the short lived autofluorescence which is generated from autofluorophores in a sample when excited by a light source and the relatively long lived fluorescence which may arise from excitation of synthetic fluorophores, one strategy is to use a light source with a very rapid decay profile. In this way, the excitation light decays rapidly and consequently the autofluorophores will be excited over a relatively short time period. Once the autofluorescence has decayed to a sufficiently low level, fluorescence from the synthetic fluorophores may be still be detectable. Thus if detection is commenced only once the autofluorescence has reduced to the sufficiently low level (i.e. after a suitable gate delay), autofluorescence may be separated out from the fluorescence from synthetic fluorophores, enabling detection of only the fluorescence from synthetic fluorophores. If the synthetic fluorophores are attached selectively to a species of interest, this enables detection, and optionally counting, of those species of interest. Another strategy is to use a high sensitivity detector. In this way, the residual fluorescence from synthetic detectors may be detected even after a relatively long delay to allow decay of autofluorescence. By combining these strategies, using a high sensitivity detector and a rapid decay excitation light source, the inventors have found that the sensitivity and selectivity of fluorescence detection may be significantly improved, while avoiding at least some of the disadvantages of the prior art. Suitable fluorophores for use in conjunction with the present invention are discussed for example in WO 2005/085193, the contents of which are incorporated herein by cross-reference. The present invention may be particularly suitable for use in conjunction with fluorophores with short fluorescence lifetimes, for example between about 30 and 120 microseconds (or between about 30 and 100, 30 and 80, 30 and 50, 50 and 120, 80 and 120, 100 and 120, 50 and 100, 50 and 75 or 75 and 100 microseconds, or with fluorescence lifetimes about 30, 40, 50, 60, 70, 80, 90, 100, 110 or 100 microseconds) such as fluorophores comprising palladium or platinum. This may be due to the shorter gate delay available in the present invention. Metalloporphyrins such as palladium and platinum coproporphyrin labels may for example be used, and are described in de Haas, R. et al, *Journal of Histochemistry and Cytochemistry*, 47(2), 1999, 183-196 (http:/www.jhc.org), the contents of which are incorporated herein by cross-reference.

The light source of the system may have a faster decay time than conventional light sources. The detector of the system may provide higher sensitivity than conventional detectors. The fluorescence systems of the present invention may have improved detection sensitivity compared to conventional systems. The improved light source and/or the improved detector may be no more expensive than existing light sources and/or detectors, and may be less expensive. The system may have no shutter for preventing a light emission from the light source from reaching the detector during a period when the detector is capable of detecting light. They may have circuitry for providing a gate delay between the end of a light pulse from the light source and the commencement of detection by the detector, so that the light emission has decayed by the time detection is commenced, and the light emission is not detected by the detector. The systems may be capable of rapid off-chip integration of signals from the detector.

The principle underlying TRFM is illustrated in FIG. 1, which shows a graph having time on the X-axis and light intensity the Y-axis. A TRFM cycle begins with a short pulse of light, idealized here as a square wave, that excites fluorescence from a probe fluorophore (such as a lanthanide chelate) as well as any autofluorophore that may be present. After the light pulse, autofluorescence decays within nanoseconds, as shown in the expanded view, however the fluorescence arising from the probe fluorophore persists for hundreds of microseconds longer. The time-resolving phase corresponds to the gate-delay period that occurs between the end of the excitation pulse and start of the signal acquisition period. The length of the signal acquisition period depends on the fluorescence lifetime of the probe fluorophore and this varies within different solvent environments. The minimum gate-delay duration, for most TRFM instruments, is controlled by the decay rate of the excitation light pulse. In the present specification, the distinction is drawn between "fluorescence" which is emitted by fluorescently labeled species, and "autofluorescence" (or "intrinsic fluorescence") which is emitted by naturally fluorescent materials that have not been labeled with a fluorophore but which occur in a sample under examination.

In the systems disclosed herein, the detector may capture a single excitation event following a short gate-delay and a time-resolved fluorescence image may then be stored externally. This operation may be repeated at high speed, and the images averaged in real-time to provide a final image. This may obviate the need for an electronic or mechanical shutter to block light from the light source from reaching the detector during the excitation phase and may maximize optical transfer efficiency of fluorescence to the image sensor. This technique is made feasible by the high gain of the detectors described herein. Thus the systems disclosed herein may have no shutter. Light emission from the light source may be prevented from directly reaching the detector during a period when the detector is capable of detecting light by control circuitry. Light emission from the excitation source may reach the detector, however control lines to the sensor are gated such that any photoelectrons generated are immediately shunted to ground and this state is maintained until the excitation pulse has terminated. This circuitry provides an appropriate gate delay between the end of a light pulse from the light source and the commencement of detection by the detector, so that the light emission has decayed by the time detection is commenced, and the light emission is not detected by the detector.

The recent availability of light emitting diodes (LEDs) that emit at 365 nm (FWHM of 10 nm), prompted evaluation for their suitability in time-resolved fluorescence applications. The fluorescence emission that is captured following the gate-delay period is typically of low intensity and image-intensifiers may be employed in conjunction with the CCD camera. Cameras equipped with image intensifiers are expensive, usually require cooling and are bulky in comparison to conventional CCD cameras. A new generation of CCD image sensor has recently become available that can multiply charge directly in the charge domain before conversion to voltage. The amount of multiplication is adjustable, depending on the amplitude of the multiplication pulses and custom CCD image sensors with gains upwards of 2000-fold are commercially available from Texas Instruments Inc. Japan (Nishi-Shinjuku Mitsui Bldg., 6-24-1 Nishi-Shinjuku, Shinjuku-ku, Tokyo 160-8366, Japan). This device function resembles the function of image intensifiers implemented in solid state. When cooled, the charge amplifying CCD can integrate and amplify the low intensity fluorescence signal to a useful level. The invention disclosed herein describes, in certain embodiments, the modification of a commercial fluorescence microscope to utilize an inexpensive UV LED as the excitation source, in conjunction with a charge multiplying CCD image sensor to capture time-resolved fluorescence.

Autofluorescence is a significant problem that can hinder the detection of immunofluorescently labelled organisms using fluorescence microscopy. The real-time, time-resolved fluorescence microscope disclosed here is intended to suppress intrinsic fluorescence (autofluorescence) in microscopy samples with no capture latency. The instrument is designed to permit the transmission of only long-lived fluorescence to a detector (for example an eye or electronic camera) whilst strongly suppressing short-lived autofluorescence. The end result is an enhancement of probe fluorescence over non-specific autofluorescence.

The LEDs of the present invention are capable of providing radiation in the UV range, commonly in the near UV range. The wavelength generated by the LEDs may be in the range between about 275 and 395 nm, or between about 300 and 400 nm or about 325 and 400 nm or about 350 and 400 nm or about 375 and 400 nm or about 300 and 375 nm or about 300 and 350 nm or about 325 and 375 nm or about 350 and 375 nm, and may be about 300, 305, 310, 315, 320, 325, 330, 335, 340, 345, 350, 355, 360, 365, 370, 375, 380, 385, 390, 395 or 400 nm. For example a gallium nitride (GaN) LED may provide light at about 365 nm, and a GaN/silicon carbide LED may provide light at about 395 nm. The FWHM (full width at half maximum) of the light emission of the LED may be between about 5 and 20 nm, or between about 5 and 15 nm or about 5 and 10 nm or about 10 and 20 nm or about 15 and 20 nm or about 10 and 15 nm, and may be about 5, 10, 15 or 20 nm. The wavelength of the light emission may be suitable for exciting fluorescence in a species labeled by a fluorescent label. Other LEDs that may be used in the present invention include InGaN (indium gallium nitride), InN (indium nitride), AlGaN (aluminium gallium nitride) or InAlGaN (indium aluminium gallium nitride) LEDs. Laser diodes are also available, for example from Nichia Corporation, which provide a wavelength of about 405 nm. Examples of UV LEDs based on InGaN available from Nichia Corporation (5-34-7 Shiba Minato Tokyo Japan 108-0014) are LED types NCCU001 (peak spectrum 380 nm) and NCCU033 (peak spectrum 365 nm).

The optical output power of the LED may be greater than about 2 mW, or greater than about 3, 4, 5, 10, 20, 30, 40, 50, 60, 70, 80, 90, 100, 150, 200, 250, 300, 350 or 400 mW, and may be about 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 220, 240, 260, 280, 300, 320, 340, 360, 380, 400 or more than about 400 mW. Stronger excitation results in more effective activation of the fluorophore. This is of special significance considering the difference in the peak wavelength sensitivity of the time-resolvable fluorophore and the LED wavelength (337 nm and 365 nm respectively).

The LED may comprise a single facet or multiple facets. For example certain LEDs from Nichia comprise a chip about 1 mm square that is comprised of 5×5 gallium nitride facets. This may result in an intensity pattern on the sample. The system may therefore comprise a beam homogeniser, together with suitable optics to overcome or at least partially eliminate the intensity pattern, or the computer or the electronics may have software to ameliorate, overcome or at least partially eliminate the intensity pattern. Such measures may be unnecessary if the LED comprises a single monolithic gallium nitride chip.

There are many fluorescent labels known in the art, and they may for example comprise fluorophores comprising lanthanide ions complexed with substituted terphenyl moieties. Such fluorophores may have maximum absorption (ie maximum extinction coefficient) for example around 340 nm, however due to the breadth of the absorption, the extinction coefficient at the LED wavelength of about 365 nm may be about 40% of the maximum extinction coefficient. This may provide sufficient fluorescence for the fluorescence detection system of the present invention. The ratio of the extinction coefficient at the wavelength of the LED light emission to the maximum extinction coefficient of the fluorophore may be between about 10 and 100%, or between 10 and 80% or 10 and 60% or 10 and 40% or 20 and 100% or 40 and 100% or 60 and 100% or 20 and 90% or 30 and 80% or 30 and 60%, and may be about 10, 20, 30, 40, 50, 60, 70, 80, 90 or 100%. The greater this ratio, the more sensitive is the fluorescence detection system.

Commonly in time resolved fluorescence microscopy, a sample is irradiated by a light emission from a light source, thereby exciting fluorescence in the sample. Whereas species that have been intentionally labelled with an appropriate fluorophore may be detected by detecting the fluorescence, other species such as algae that have not been so tagged (ie autofluorophores) may also fluoresce. However the fluorescence from an intentionally tagged species typically decays over a far longer period than does the fluorescence from autofluorophores. Typically fluorescence from labelled species may decay over a period of greater than about 50 microseconds, or greater than about 100, 150, 200, 300, 400, 500, 600 or 700 microseconds, or between about 50 and 750 microseconds, or between about 100 and 750 microseconds, or about 200 and 750 microseconds or about 500 and 750 microseconds or about 50 and 500 microseconds or about 50 and 250 microseconds or about 50 and 100 microseconds or about 100 and 600 microseconds or about 100 and 500 microseconds or about 200 and 500 microseconds or about 200 and 350 microseconds, or over a period of about 50, 100, 150, 200, 240, 250, 300, 350, 400, 500, 550, 600, 640, 650, 700 or 750 microseconds. However fluorescence from an autofluorophore may decay over a period of less than about 1 microsecond, or less than about 500, 200, 100, 50 or 20 ns, or between about 1 and 1000 ns, or 5 and 1000, and 1000, 50 and 1000, 100 and 1000, 500 and 1000, 1 and 500, 1 and 200, 1 and 100, 1 and 50, 1 and 20, 1 and 10, 10 and 500, 50 and 200 or 50 and 100 ns, or about 1, 2, 3, 4, 5, 6, 7, 8, 9, 10, 15, 20, 25, 30, 35, 40, 45, 50, 60, 70, 80, 90, 100, 200, 300, 400, 500, 600, 700, 800, 900 or 1000 ns. Thus by inserting a gate-delay following a light emission pulse from the LED before detection commences, it may be possible to distinguish between unwanted fluorescence and fluorescence from labelled species. Clearly it is desirable for the decay of light emission from the light source to be rapid, since light emission from the LED after the nominal end of the pulse (i.e. during the decay time of the light emission pulse) may cause residual fluorescence from autofluorophores to extend beyond the gate-delay. Clearly also it is desirable for the gate-delay to be as short as possible, consistent with sufficient reduction in unwanted fluorescence, so that the fluorescence from labelled species is as intense as possible during the detection period. The delay before detection commences (the gate-delay) may be less than about 20 microseconds, or less than about 15, 10, 5, 2, or 1 microseconds or less than about 900, 800, 700, 600, 500, 400, 300, 200, 200, 100 or 50 ns, and may be between about 10 microseconds and 10 ns, or between about 10 microseconds and 100 ns, 10 microseconds and 500 ns, 10 and 1 microseconds, 10 and 5 microseconds, 8 microseconds and 500 ns, 5 microseconds and 500 ns, 2 microseconds and 500 ns, 1 microsecond and 10 ns, 500 and 10 ns, 100 and 10 ns, 5 microseconds and 500 ns, 8 and 1 microseconds or 5 and 1 microseconds, and may be about 10, 50, 100, 250, 500 or 750 ns or about 1, 2, 3, 4, 5, 6, 7, 8, 9, 10, 15 or 20 microseconds. The gate delay may be sufficiently long that, after the gate delay, the fluorescence is distinguishable from the autofluorescence. The gate delay may be sufficiently long that, after the gate delay, the ratio between the maximum intensity of the fluorescence and the maximum intensity of the autofluorescence is greater than about 1.5 to 1, or greater than about 2, 3, 4, 5, 6, 7, 8, 9, 10, 15, 20, 30, 40, 50, 100, 150, 200, 300, 400, 500, 1000, 1500, 2000, 2500, 3000, 3500, 4000, 4500 or 5000 to 1. The ratio may be between about 1.5 and 5000 to 1, or about 15 and 1000 or about 1.5 and 500 or about 1.5 and 100 or about 1.5 and 50 or about 10 and 5000 or about 100 and 5000 or about 100 and 5000 or about 1000 and 5000 or about 10 and 2000 or about 100 and 1000 to 1, and may be about 1.5, 2, 3, 4, 5, 6, 7, 8, 9, 10, 15, 20, 30, 40, 50, 60, 70, 80, 90, 100, 150, 200, 300, 400, 500, 1000, 1500, 2000, 2500, 3000, 3500, 4000, 4500 or 5000 to 1. A pulse of light emission from an LED is triggered by current flowing through the LED. Thus the duration of a pulse corresponds to the duration of the current flow. Following cessation of current flow, which may be regarded as the end of the light pulse, light emission from the LED will decay over a period of time. The decay of a light pulse emitted by the LED may require less, than about 10 microseconds, or less than about 8, 5, 2 or 1 microseconds, or less than about 750, 500, 250, 100 or 50 ns, or between about 10 ns and about 10 microseconds or between about 1 and about 10 microseconds or between about 2 and about 10 or about 5 and about 10 microseconds, or between about 100 ns and about 1 microsecond, or between about 500 ns and about 1 microsecond, or between about 10 and about 500 ns or between about 10 and about 100 ns or between about 500 ns and about 10 microseconds or between about 500 ns and about 8 microseconds or between about 500 ns and about 5 microseconds, and may require about 10, 50, 100, 200, 300, 400, 500, 600, 700, 800 or 900 ns or about 1, 2, 3, 4, 5, 6, 7, 8, 9 or 10 microseconds. For the present purpose the decay of a light pulse may be considered to be the time for the pulse to reduce to 15% of its original intensity, or to 10, 9, 8, 7, 6, 5, 4, 3, 2, 1, 0.5, 0.1, 0.05 or 0.01% of its original intensity. The light source may be a low voltage light source, and may have an operating voltage of between about 1 and 20V, or about 1 and 10, 1 and 5, 1 and 2, 2 and 20, 5 and 20, 10 and 20 or 5 and 10V, and may have an operating voltage about 1, 1.5, 2, 2.5, 3, 3.5, 4, 4.5, 5, 6, 7, 8, 9, 10, 11, 12, 13, 14, 15, 16, 17, 18, 19 or 20V. The power of the LED may be between about 1 mW and 1 W, or between about 1 and 500 mW, or between about 1 and 200, 1 and 100, 1 and 50, 1 and 20, 10 and 10, 1 and 5, 10 and 1000, 100 and 1000, 500 and 1000, 10 and 500 or 50 and 200 mW, and may be about 1, 1.5, 2, 2.5, 3, 3.5, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900 or 1000 mW. The power of the LED may be sufficiently low that it does not photobleach the fluorescent dye under its conditions of use.

The emission from the light source may be pulsed and the duration of the pulse may be between about 10 ns and 500 microseconds, or between about 10 ns and 200 microseconds, 10 ns and 100 microseconds, 10 ns and 10 microseconds, 10 ns and 1 microsecond, 10 and 500 ns, 10 and 100 ns, 100 ns and 200 microsecond, 1 and 200 microseconds, 10 and 200 microseconds, 50 and 200 microseconds, 1 and 100 microseconds or 10 and 100 microseconds, and may be about 10, 50, 100, 250, 500 or 750 ns, or about 1, 5, 10, 20, 30, 40, 50, 60, 70, 80, 90, 100, 120, 140, 160, 180, 200, 250, 300, 400 or 500 microseconds. The time between pulses may be between about 1 microsecond and 1 ms, or between about 1 and 500, 1 and 200, 1 and 100, 1 and 50 or 1 and 10 microseconds, or between about 100 microseconds and 1 ms, 500 microseconds and 1 ms or 100 and 500 microseconds and may be about 1, 5, 10, 50, 100, 250, 500 or 750 microseconds, or about 1 ms. The use of an LED light source according to the invention may obviate the need for a filter such as an IR filter, which is commonly used in time resolved fluorescence microscopy in conjunction with a flash lamp light source. Following a gating-delay, the detector may be triggered to detect fluorescence from the sample for a period of between about 10 and 1000 microseconds, or between about 10 and 500, 10 and 200, 10 and 100, 10 and 50, 50 and 1000, 100 and 1000, 500 and 1000, 50 and 500 or 50 and 200 microseconds, and may be for a period of about 10, 20, 30, 40, 50, 60, 70, 80, 90, 100, 150, 200, 250, 300, 400, 500, 600, 700, 800, 900 or 1000 microseconds. In order to acquire an image, multiple cycles may be performed, each comprising generating a light pulse, applying a gate delay, and detecting a fluorescence. To acquire a single image, between 1 and 1000 cycles may be performed, or between about 1 and 500, 1 and 200, 1 and 100, 1 and 50, 10 and 1000, 100 and 1000, 500 and 1000, 50 and 500, 50 and 200, 100 and 500 or 200 and 300 cycles, and about 1, 2, 3, 4, 5, 10, 20, 50, 100, 150, 200, 250, 255, 300, 400, 500, 600, 700, 800, 900 or 1000 cycles may be performed.

A means to improve the sensitivity of a fluorescence detection system according to the present invention is to improve the sensitivity of the detector of the system. The detector may be any suitable detector for detecting fluorescence, and may be for example a CCD, CMOS, a photomultiplier, a solid state source or some other electronic detector, a light sensitive film such as photographic film, or it may be a human eye. The CCD may have very low noise, very high sensitivity and electrically variable charge domain gain. The CCD may be a low resolution CCD, since the fluorescence detection system may be used for counting species rather than for imaging them. The CCD may have on-chip amplification, and the amplification may be greater than 20, or greater than 30, 40, 50, 60, 70, 80, 90, 100, 200, 500 or 1000, and may be between about 20 and 1000 or between about 20 and 500, 20 and 200, 20 and 100, 20 and 50, 50 and 1000, 100 and 1000, 500 and 1000, 30 and 500, or 50 and 200, and may be about 20, 30, 40, 50, 60, 70, 80, 90, 100, 150, 200, 250, 300, 350, 400, 450, 500, 600, 700, 800, 900 or 1000. The CCD may be cooled. A suitable CCD for use in the present invention may be for example Texas Instruments "Impactron" CCD. The detector may be capable of detecting fluorescence in the visible range, that is in the range of about 400 to 700 nm wavelength, or between about 400 and 550 or 550 and 700 or 500 and 600 or 600 and 700 nm, and may be capable of detecting fluorescence having one or more wavelengths selected from about 400, 450, 500, 450, 600, 650 and 700 nm. A suitable europium-based fluorophore which may be used in conjunction with the present invention may provide fluorescence at about 617 nm. A system according to the present invention may have more than one detector, and may have more than one type of detector. The detectors may be configured to detect simultaneously, or there may be a switching device for switching between them.

A fluorescence detection system according to the present invention may comprise a magnifying device such as a microscope, a microscope objective lens, a magnifying lens or some other magnifying device. The magnification obtainable from the magnifying device may be between about 2× and 2000×, or between about 2× and 100×, 2× and 500×, 2× and 100×, 2× and 50×, 100× and 2000×, 500× and 1000×, 500× and 2000×, 10× and 1000× or 100× and 500×, and may be about 2, 3, 4, 5, 10, 20, 30, 40, 50, 100, 150, 200, 250, 300, 350, 400, 450, 500, 600, 700, 800, 900, 1000, 1250, 1500, 1750 or 2000×.

A fluorescence system according to the present invention may have an eyepiece, or a pair of eyepieces, for viewing a sample visually. It may additionally comprise means to prevent harmful radiation reaching the eyepiece(s), so as to prevent harm to an observer. The means may comprise a shutter, or a filter, and may operate automatically or manually or may be permanently in place.

The present invention also encompasses a kit for modifying a fluorescence microscope, as well as a method for modifying a fluorescence microscope by fitting such a kit. Fluorescence microscopes are a commonly used item of laboratory equipment, particularly in biological laboratories. The present invention provides a means to modify such microscopes using a relatively inexpensive kit in order to provide a more effective detection system. The kit may comprise for example a filter-box assembly, an example of which is shown diagrammatically in FIG. 2.

Figure 2:
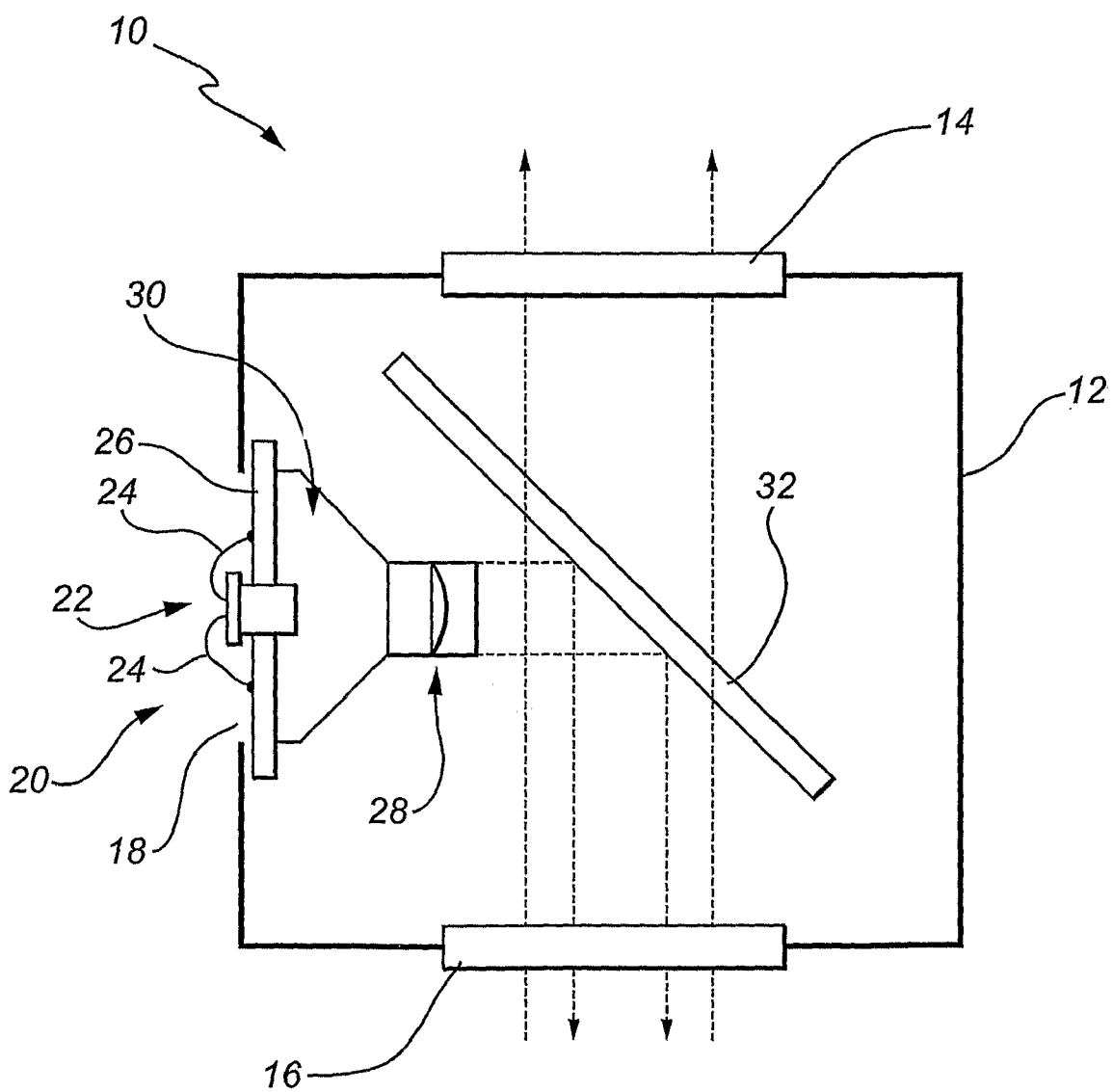
FIG. 2 is a diagrammatic representation of an LED filter box assembly which may form part of a fluorescence detection system according to the present invention.

With reference to FIG. 2, filter-box assembly 10 comprises housing 12 fitted with emission port 14 and excitation port 16. Housing 12 also has hole 18 into which is fitted source assembly 20. Source assembly 20 comprises LED 22, which is capable of generating UV light of a wavelength capable of exciting fluorescence in an species labelled with a target fluorescent label (commonly in the range of about 350 to 400 nm), and is connected by electrical connections 24 to printed circuit board 26, which is capable of controlling LED 22. Source assembly 20 also has collimating lens 28 mounted in conical lens support 30. Dichroic mirror 32 is provided to direct UV light from LED 22 towards excitation port 16. Mirror 32 is highly reflective towards the frequency of UV light emitted by LED 22, and is highly transmissive towards the frequency of fluorescence emitted by a sample on excitation with the UV light emitted by LED 22. Emission port 14 is also highly transmissive towards the frequency of fluorescence emitted by a sample on excitation with the UV light emitted by LED 22, and excitation port 16 is highly transmissive towards both the frequency of UV light emitted by LED 22 and the frequency of fluorescence emitted by a sample on excitation with the UV light emitted by LED 22.

A beam homogenizer may be incorporated into the optics to avoid the formation of an intensity modulated pattern on the sample arising from the nature of the LED die manufacture. The LED die is in the form of a 5×5 matrix of interconnected chip elements (facets).

In operation, circuit board 26 controls UV LED 22 via connections 24 to provide a UV emission, which passes through lens support 30 to collimating lens 28, which collimates the UV emission. The collimated UV emission passes to mirror 32 which reflects it through excitation port 16 to a microscope objective lens (not shown), which passes it to a sample (also not shown). The UV emission stimulates fluorescence within the sample, and a fluorescence emission passes through the microscope objective lens, which magnifies it, and through excitation port 16 to dichroic mirror 32. Dichroic mirror 32 is transparent to the wavelength of the fluorescence emission and transmits it through emission port 14 to a detector, for example a CCD, or an eyepiece (not shown).

For operation by means of time resolved fluorescence microscopy, a CCD detector may be located so as to receive a signal passing through emission port 14, and is coupled to circuit board 26. In this case circuit board 26 causes UV LED 22 to provide pulsed UV emission. A pulse of UV emission, which may be between about 50 and 200 microseconds in duration, is directed from LED 22 to the sample as described above, causing a fluorescent emission to pass to the detector. In this case circuit board 26 maintains the detector in a non-operational condition (ie not capable of detecting a signal) until a fixed gate-delay after the end of the UV emission pulse. The gate-delay is set such that autofluorescence from unlabelled species in the sample has decayed by the end of the delay time, and may be between about 1 and 5 microseconds. At the end of the delay time, circuit board 26 triggers the detector to detect a fluorescence signal, so that fluorescence emissions from labelled species, which have longer fluorescence lifetimes than autofluorophores, will be detected. At the end of a suitable detection period, which may be between about 10 and 800 microseconds, the circuit board 26 returns the detector to a non-operational condition prior to triggering UV LED 22 to emit a further pulse of UV light. The sequence described above is then repeated for each pulse of UV emission.

A disadvantage of TRFM designs of the prior art is the relatively long decay time of the flashlamp plasma, which results in a decrease in the signal-to-noise ratio (S/N) if short gate-delay periods are employed. The gate-delay period is the time-resolving phase of TRFM during which the short lived fluorescence is permitted to decay. A problem with flashlamps is the presence of glowing plasma after the main arc discharge, which persists for hundreds of microseconds and prevents capture of fluorescence from synthetic probes until the flashlamp plasma has decayed substantially. This extended gate delay period of 50 μs results in a loss of about 20% of the initial fluorescence intensity emitted by the synthetic probes, and an excitation source that could be extinguished completely within 5 μs would permit capture of more than 98% of the initial fluorescence emission. A new source of UV illumination with the desired characteristics has recently become available. Light emitting diodes (LEDs) with a peak wavelength of about 365 nm are available from Nichia Corporation of Japan and these may be switched, persistence free, within microseconds.

The most costly component of TRFMs of the prior art is the image capture device, a time-gated microchannel plate image-intensifier coupled to a cooled high resolution CCD camera. The DicamPro camera costs about $70,000 and a less costly replacement would be preferred. A recent innovation from Texas Instruments (Dallas, Tex., USA) has resulted in a CCD element with on-chip amplification that permits image-capture at very low light levels. In the present invention, the CCD may be operated in "single-shot" mode to capture a single excitation event following a short gate-delay period (5 μs) and a time-resolved fluorescence image is then stored externally in high speed memory. This operation is repeated at high speed, for example every 300 to 500 μs, and each frame is digitally averaged in real-time to provide the final image. This technique avoids the requirement for an electronic shutter to block light from reaching the camera during the excitation phase and maximizes optical transfer efficiency of fluorescence to the image sensor. This technique is made feasible by the high gain of a detector such as the Texas Instrument CCD image sensor described herein.

A camera employing this CCD element is available commercially from a number of suppliers, however the present inventors have the capacity to interface the chip with custom developed electronics to avoid the requirement to shutter the image sensor during the excitation phase. This provides a TRFM that is capable of operating in real-time or near real-time (for example with about 100 ms latency) to suppress autofluorescence. This provides a significant advantage over the current TRFM design that requires a 7-second acquisition period for each frame analysed.

Novel features of the invention disclosed herein include:
  The use of ultra violet emitting LEDs as an excitation source for a time-domain TRFM. These devices have not previously been commercially available and are still classified as "engineering samples" for development purposes.
  The recent availability of the Texas Instruments "Impactron" process CCD chips has enabled their incorporation into TRFM designs. This CCD element is still unavailable to in Australia and further value will be added by designing the electronics to suit the application for which the chip is intended.

EXAMPLE

The recent availability of light emitting diodes (LEDs) that emit at 365 nm (FWHM of 10 nm), prompted evaluation for their suitability in time-resolved fluorescence applications. LEDs are easily powered and have the advantage of nanosecond switching speeds, however the emission wavelength longer than is optimal (337 nm). Nevertheless, a UV LED was employed as the excitation source to replace the flashlamp in a lab-built TRFM. The LED (type NCCU033, rated at 100 mW; Nichia Corp, Japan) was adapted to fit the filter-box housing of a fluorescence microscope (Axioscop; Zeiss Instruments) and used to excite fluorescence from fluorescently labelled Giardia cysts spiked into a 10,000:1 water concentrate that was strongly autofluorescent. The LED was pulsed for a 100 μs duration at a repetition rate of 500 Hz with a peak current of 793 mA. The narrow line width of the LED UV emission enabled removal of the excitation filter and emission filter, resulting in a significant improvement in sensitivity of the TRFM. The LED type NCCU033 is an InGaN LED and has the following specifications: pulse forward current maximum 1000 mA, pulse width ≦10 ms, duty ≦1/10; operating temperature −10-85° C.; peak wavelength between 360 and 370 nm, typically about 365 nm, spectrum half width about 8 nm; optical power output 130-154 mW (Rank P3), 110-130 mW (Rank P2), 92-110 mW (Rank P1).

A 10,000:1 water concentrate sample was spiked with immunofluorescently labelled Giardia cysts to evaluate the effectiveness of the NCCU033 LED as an excitation source for TRFM. A water concentrate may be prepared by collecting all microscopic particles larger in diameter than about 1 micron from a large volume of water, typically 10 to 100 litres. The isolation process may employ filtration or flocculation techniques and the latter method was used to prepare the 10,000:1 concentrate used here. The water concentrate contained strongly autofluorescent algae, mineral particles and organic debris that made the detection of fluorescently labelled target a difficult task using conventional fluorescence microscopy. The Giardia cysts were labelled with an immunoconjugate of BHHST, a less hydrophobic derivative of BHHT that has recently been reported (Connally, Australian Patent Application No. 2004901196). Image a in FIG. 3 was acquired using the LED as the excitation source and with the TRFM equipped with a longpass filter (greater than 90% transmission at wavelengths longer than 420 nm). The window effect that can be seen in image a is a result of the image of the LED die matrix being superimposed on the object at the point of focus. This artefact can be removed by homogenizing the LED beam using conventional optical methods (frosted glass, lenticular array etc.) before it reaches the microscope objective. The image intensifier was operated at low gain (5%) and the image was constructed from a total of 255 image acquisitions (loop count of 255). Pixel binning was enabled to bin four pixels into 1. Pixel binning adds the charge accumulated in a 2×2 array of pixels so that intensity is increased four-fold, however resolution is halved in both the horizontal and vertical axes. Image b of FIG. 3 was captured using an image-intensifier gain of 50%, 2×2 pixel binning, a loop count of 255 and a gate-delay of 5 µs. The Giardia cysts had been labelled with a immunoconjugate estimated to have a fluorophore to protein ratio of 24. Labelling of the cysts had been performed approximately 14 months beforehand and the cysts had been stored in bicarbonate buffer at 4 degrees Celsius since that time. FIG. 4 shows image intensity graphs corresponding to the images of FIG. 3.

Electronic Drive for the LEDs

Figure 5:
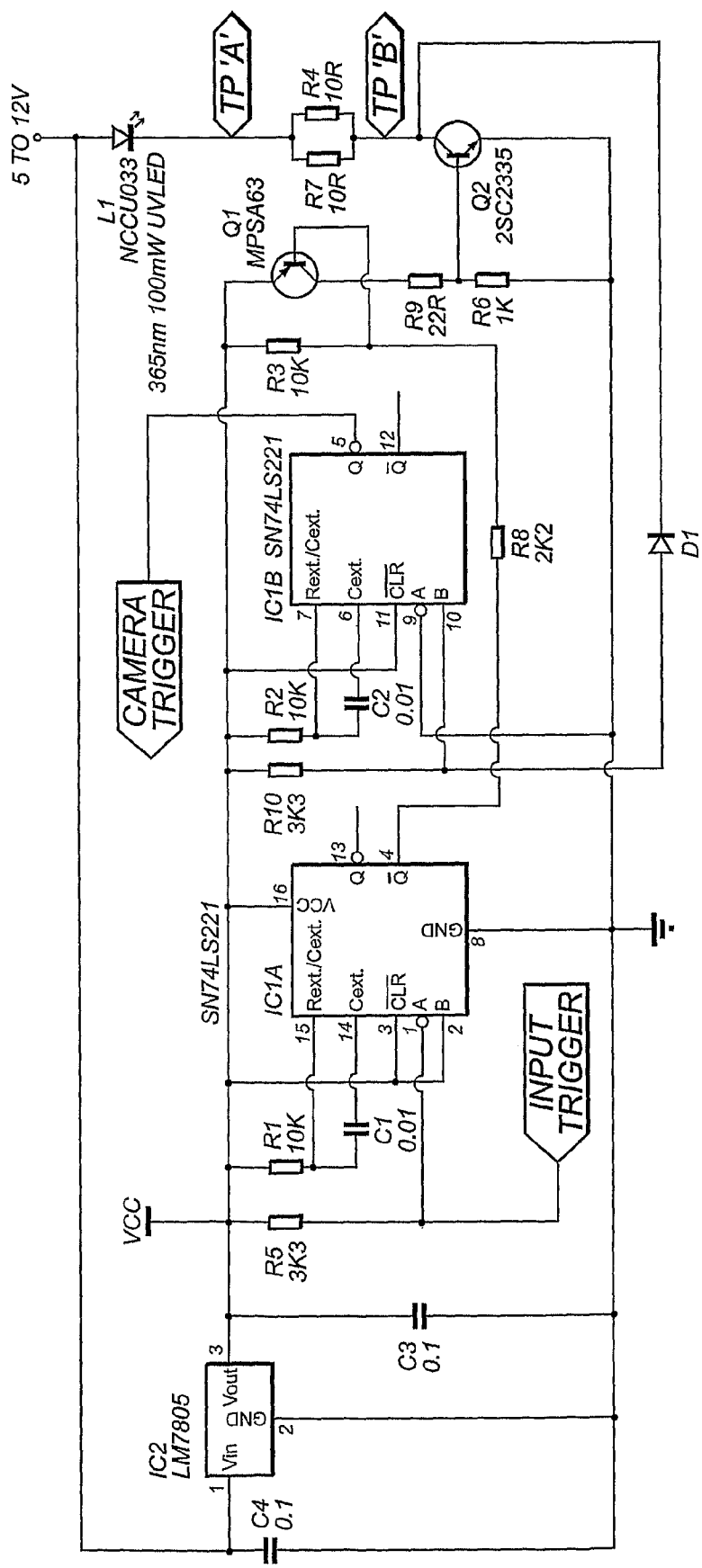
FIG. 5 shows a circuit diagram of a dual monostable multivibrator package for driving the LED and triggering the detector in a TRFM according to the invention.
Figure 6:
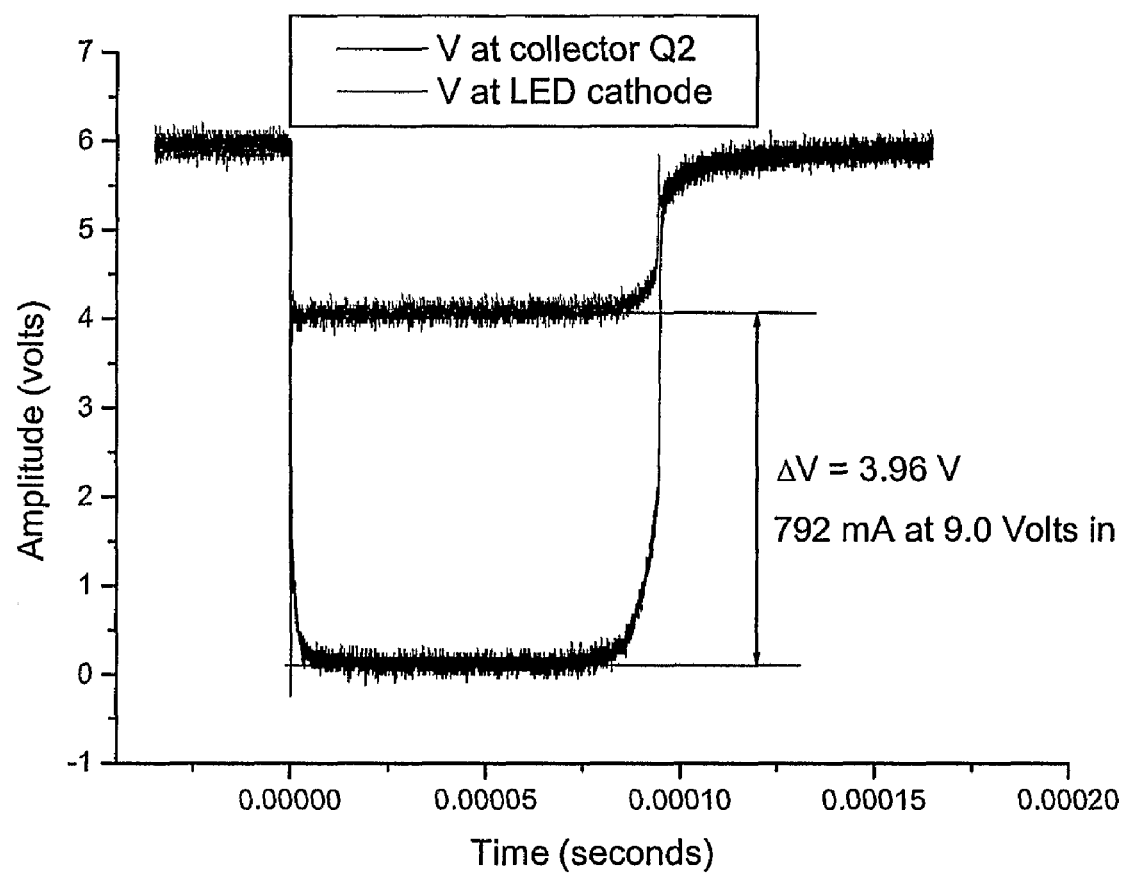
FIG. 6 shows oscilloscope waveforms captured at the test points marked TP 'A' and TP 'B' of the circuit of FIG. 5, showing the voltage difference with respect to ground for each point, in which the waveforms are overlaid to show the voltage difference across the load resistors (R4 and R7) of 3.96 volts that corresponds to a peak current through the resistors (and thus the LED) of 792 mA.
Figure 7:
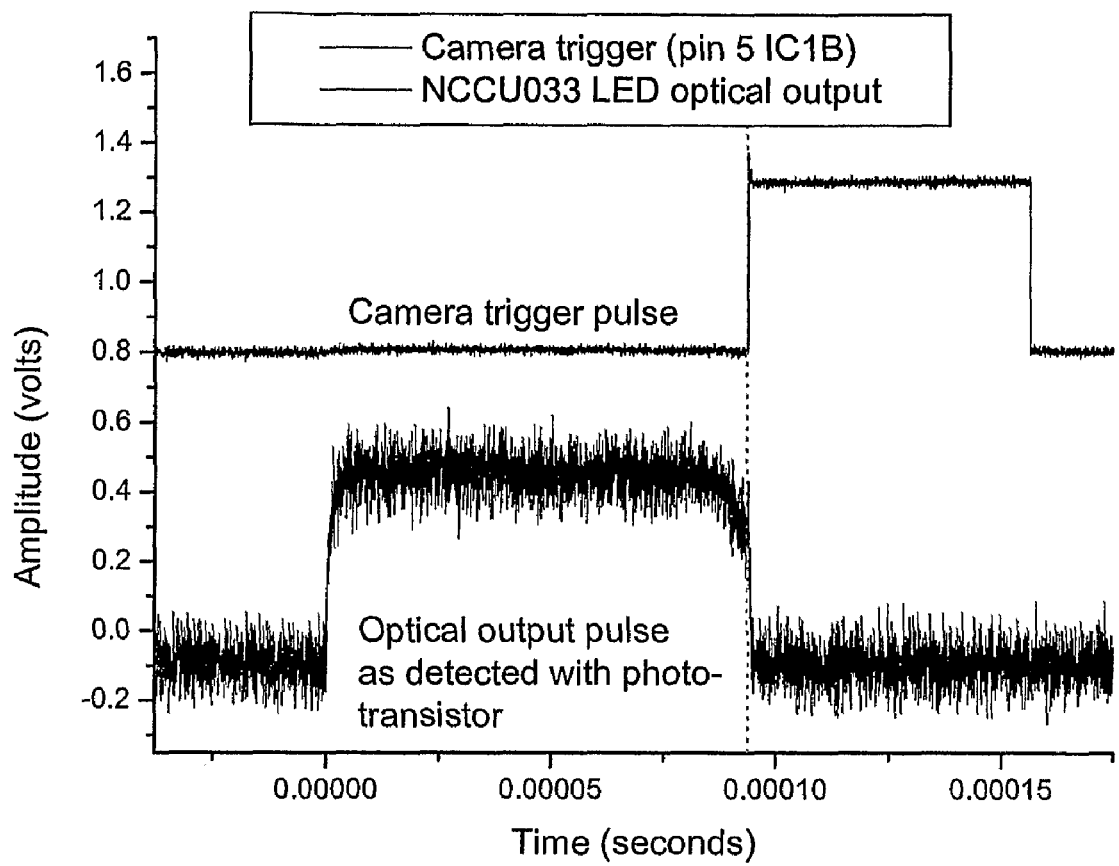
FIG. 7 shows a graph illustrating the relationship between the optical output pulse of the LED as detected by a phototransistor and the initiation of the camera trigger pulse, in which the camera trigger pulse follows the optical output pulse with a delay measured in nanoseconds.

A dual monostable multivibrator package (74LS221) was used to provide the two pulse outputs used to drive the LED and to trigger the camera. A circuit diagram for this is shown in FIG. 5. An external square wave generator operating at a frequency of approximately 1 kHz is used to drive the monostable into conduction. The falling edge of the input trigger (pin 1 of IC1A) initiates a 100 µs negative going output pulse on pin 4 that causes the transistor Q1 to conduct and consequently drive the output transistor Q2 into conduction and switch the LED on. At the completion of the 100 µs timing cycle of IC1A, Q2 is turned off and the voltage at pin 10 of IC1B that was held low via D1 returns to a logic HIGH state and initiates a second 100 µs pulse that is used to trigger the camera electronics. The start of the gate-delay period corresponds to the time that the camera trigger is driven to a logic high and the duration of the gate-delay period is controlled externally within the camera electronics or firmware and not affected by the duration of the camera trigger pulse. With an input voltage of 9.0V, the current through L1 of FIG. 5 was 793 mA, and this was reduced to 560 mA when the voltage was dropped to 7.6V. The output pulse width was 102 µs. The relationship between pulses is illustrated by FIG. 7. The delay between the falling edge of the LED drive and the rising edge of the camera trigger pulse is very short (~4 ns) and both pulses have a duration of approximately 90 µs. The software supplied with the camera permits a programmable gate-delay to be introduced from the start of the rising edge of the camera trigger pulse thus eliminating any requirement for the electronics hardware to support this feature. The oscilloscope waveforms shown in FIG. 6 were obtained by sampling voltages at the points marked TP 'A' and TP 'B' on the circuit diagram shown in FIG. 5. The instantaneous peak current was deduced by noting the voltage difference across the load resistor (comprised of resistors R4 and R7). Using this technique, peak current was measured to be 793 mA with an input voltage of +9.00 volts at the LED anode. The images shown in FIG. 3 were acquired using the LED excitation source and an input voltage of 9.00 volts. All waveforms were captured with a Tektronix 500 MHz digital oscilloscope (TDS520). The oscilloscope waveforms shown in FIG. 7 were captured to illustrate the timing between the LED optical output pulse and the camera trigger pulse. A high-speed photo-transistor was situated close to the LED output and used to sample the optical output pulse. Although the photo-transistor had a very rapid response, it had relatively low sensitivity to the LED wavelength of 365 nm and thus a high gain setting on the oscilloscope was employed. The high gain setting resulted in an apparently noisy optical output pulse that has no significance as to the operation of the TRFM.

The power supply for the UV LED is taken from the regulated input into the voltage regulator so that current through the LED can be controlled more easily. The LED is on for a short period of 100 µs and off for a much longer period of 2 ms so that the duty rate is 1/20 and the device can tolerate much higher currents than its rated maximum (500 mA) for this short period.

The camera trigger input is designed to accept a TTL input and the output from the monostable (pin 5) was fed directly to the camera via a short (800 mm) coaxial cable. The output drive transistor is a high voltage high current device that has significant internal capacitance that delays the timing of the LED drive signal. It was found necessary to take the output signal from the collector of Q2 (via diode D1) as the trigger input into the second monostable to maintain a synchronous relationship between the termination of the optical output pulse and initiation of the camera trigger pulse.

Image Sensor

Fluorescence emitted by time-resolvable fluorophores is of low intensity and amplification of the light is necessary. Conventional charge coupled device (CCD) image sensors may be employed for the capture of the faint fluorescence if they are equipped with an image intensifier (typically 10,000-fold gain). Image intensified CCDs are relatively bulky and complex assemblies that typically cost in the region of AUD$70,000 and thus prohibit the construction of inexpensive image resolving microscopes that employ time-resolved fluorescence techniques.

A new generation of commercially available, light amplifying CCDs has recently become available that can achieve modest gains on chip (30 to 100-fold), however advanced techniques using the same process can produce image-sensors with gains of up to 2000-fold. These image-sensors are available commercially from Texas Instruments Japan). An advantage of designing a time-resolved fluorescence microscope with a charge amplifying CCD is the significant reduction in cost. A camera can be constructed at about a tenth of the cost of an image intensified CCD, and the image quality is superior, since there is no requirement to image the phosphor output of the image intensifier. Instead, the fluorescence is directly imaged onto the sensor surface at a resolution of 7.4 µm pixels (TC253SPD; Texas Instruments) compared to the 12 µm channels on a typical (Hamamatsu) microchannel plate array image intensifier (2.6-fold difference in area). Furthermore, the spectral quantum efficiency of the TC253SPD sensor is maximal (40%) at the emission wavelength of europium chelates (617 nm) whereas the S20 photocathode of the image intensifier has a quantum efficiency of less than 20% at the same wavelength. Shutter speed of the TC253SPD sensor can be precisely controlled with reference to the excitation pulse and set as short as 200 µs (1/5000 sec). This permits the sensor to be operated for a single cycle only, without a physical shutter blocking light from reaching the sensor during the excitation phase. The TC253SPD sensor multiplies charge directly in the charge domain prior to conversion to voltage. A low noise single carrier impact ionisation process is used to achieve the charge carrier multiplication (CCM). The ionisation process occurs during repeated carrier transfers through the high field regions. The multiplication gain may be adjusted by changing the amplitude to the multiplication pulses. Specifications for the TC253SPD CCD sensor include: chip size 11.68 mm (H)×12.40 mm (V), pixel size 7.4 microns (H)×7.4 microns (V); aspect ratio (H:V) 4:3; frame rate 30 Hz; data rate 12.5 MHz; shutter 1/60 second to 1/50000 second; typical sensitivity 1,200 mV/lux/sec, maximum load capacitance 6.0 pF, charge multiplication gain 1-2000 (typically about 200), excess noise factor minimum 1 (typically about 1.4), dynamic range without CCM gain 66 dB, dynamic range with CCM gain 72 dB, charge conversion gain without CCM gain 14 uV/e, signal-response delay time 16 ns, output resistance 320 ohm, Amp. Noise-equivalent signal without CCM gain 20 e, Amp. Noise-equivalent signal with typical CCM gain 1.0 e maximum, response linearity without CCM gain 1, response linearity with CCM gain 1, charge transfer efficiency 0.99994-1.0 (serial or parallel transfer), supply current without output bipolar transistor current max 4 mA (typically 2.7 mA), sensitivity with typical CCM gain 5600V/Lx*s (no IR filter), 700 V/Lx*s (with IR filter), sensitivity without CCM gain 28V/Lx*s (no IR filter), 3.5 V/Lx*s (with IR filter), saturation signal output (no CCM gain) 600 mV, saturation signal output (typical CCM gain) 1100 mV, zero input offset output 90 mV, electronic shutter capability minimum 1/5000 s, typically 1/30 s.

Texas Instruments reports that their sensor is capable of detecting single photons when cooled, or when a sufficiently short integration time is used. The analog output from the image sensor is then converted to a digital format with an 8-bit to 16-bit representation (256 to 65,535 levels) and stored in high-speed random access memory (RAM). As each frame is captured, the digitized information is electronically averaged or integrated with the previous frame in real-time using the system shown in FIG. 8 that employs a field programmable gate array (FPGA) to perform the high speed digital calculations. The advantage of employing off-chip integration results from elimination of the optical shutter that is typically necessary to prevent saturation of the image-sensor during the excitation phase when the LED is on. Currently there are no optical shutters that are capable of being switched from opaque to transmissive mode in a few microseconds. Moreover, transmission of electronic shutters (liquid crystal devices, lithium niobate etc) is typically less than 50% since they employ a shift in polarization as the switching technique and thus transmit at best a single polarized mode. Mechanical choppers afford the best modulation levels however they are limited in their speed of operation and cause uneven illumination of the sample (sunset-sunrise effect). Furthermore, optical chopper wheels can introduce vibration, especially when operated at high speeds. If however the application can tolerate these shortcomings, an electronic or mechanical shutter may be used with the TC253SPD image-sensor and integration performed for periods of up to 33 ms. This mode of operation permits the sensor to integrate fluorescence emission from a total of 82 excitation events (time regime of 100 μs excitation period and a 300 μs integration period) with a total integrated emission interval of 24 ms.

Overview of Time-Resolved Fluorescence Microscope

Figure 8:
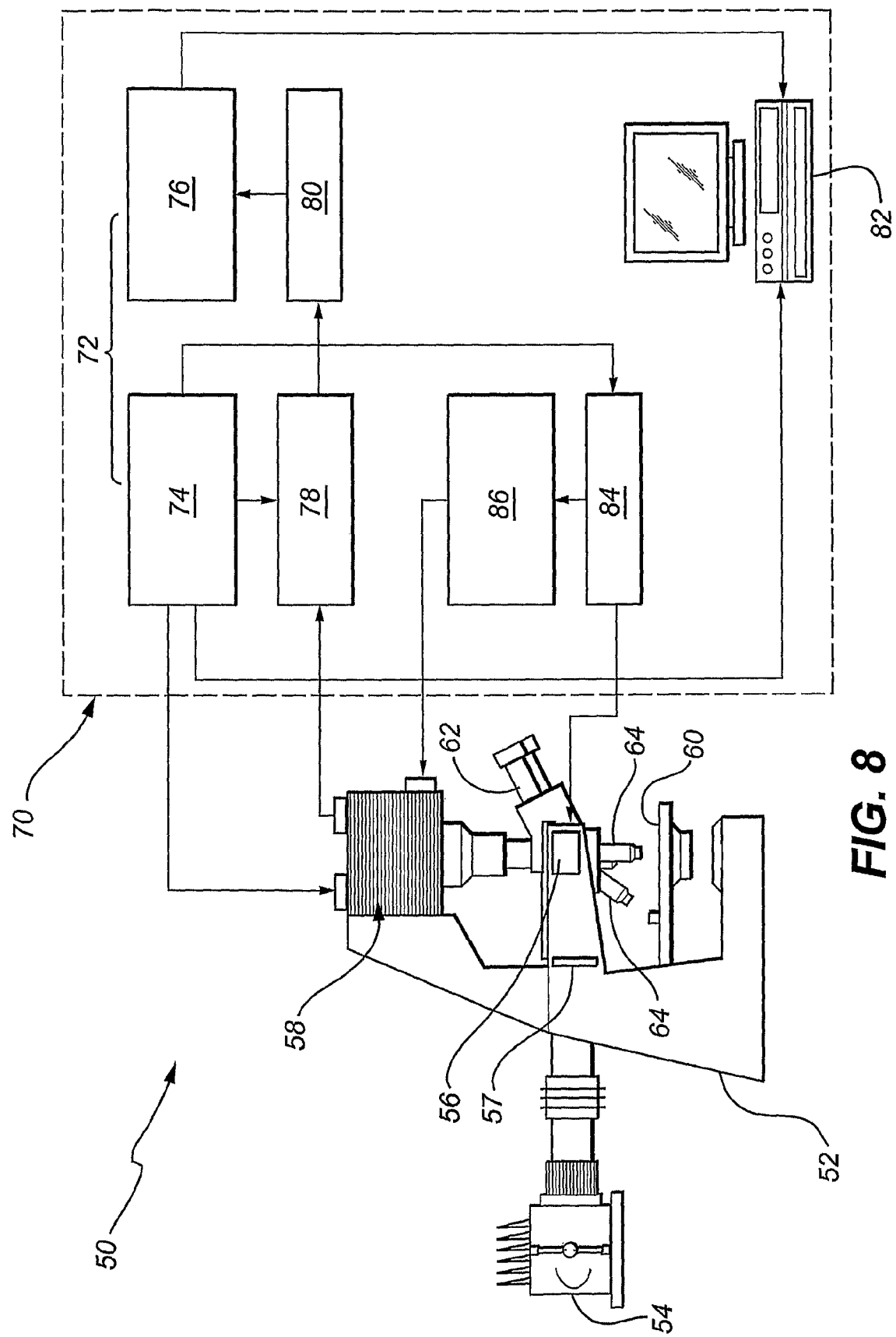
FIG. 8 shows a block diagram of a solid-state TRFM according to the present invention.

A block diagram of a design for the UV LED excited TRFM is shown in FIG. 8. The clock timing and control is based on a Field Programmable Gate Array (FPGA) since this provides the greatest flexibility in design for the system. The TC253SPD image sensor requires a complex series of voltages applied to the chip and this portion of the analogue electronics is also controlled by the FPGA.

FIG. 8 shows a block representation of the solid-state TRFM employing UV LED excitation and a charge amplifying CCD image sensor. The central control element is the field programmable gate array (FPGA) that is used to coordinate the camera control and LED excitation. Conversion of the analogue video signal to a digital (8 to 16-bit) signal facilitates image processing operations in real-time. Thus in system 50 of FIG. 8, microscope 52 is a Zeiss Axiophot microscope Microscope 52 is fitted with mercury arc lamp 54 and UV LED filter housing 56 holding a UV LED (not shown), providing two alternative sources of excitation of a sample located on stage 60. The mercury arc lamp is relatively cheap source of broad wavelength emission so that different fluorophores may be imaged in conventional epifluorescence mode. THE UV LED is capable of providing light output at about 365 nm wavelength. Microscope 52 also has eyepieces 62 for visually observing the sample (although a monocular microscope having only a single eyepiece 62 could be used), and objective lenses 64 for magnifying an image of the sample. Shutter 57 is provided to prevent illumination from arc lamp 54 from reaching the sample while an operator is observing the sample through eyepieces 62. Shutter 57 may be manually operated. Image sensor 58 is a TC253SPD Impactron CCD, located so as to receive fluorescence from a sample positioned on stage 60. Control and acquisition unit 70 is provided to control the operation and timing of the LED and of sensor 58. Unit 70 comprises FPGA 72, which has clock timing and control signal generation unit 74 for providing timing signals to sensor 58 and the LED, and also has digital signal processing (DSP) unit 76 for receiving processed data originating from sensor 58. Signal generator 74 also provides signals to analogue video processing circuit 78, which is capable of processing those signals together with signals from sensor 58 to provide an analogue signal to A/D converter 80. A/D converter 80 is capable of converting an analogue signal from processing circuit 78 into a digital signal, and supplying that digital signal to DSP unit 76 of FPGA 72. Both signal generator 74 and DSP unit 76 of FPGA 72 are capable of sending signals to computer 82 which is capable of storing, processing and presenting data. Unit 74 is also connected to UV LED drive 84, which is capable of sending control signals both directly to the LED within housing 56, and indirectly to sensor 58 via camera exposure and trigger controller 86. The components described above between signal transfers occur are connected by appropriate signal transfer cables, which may be capable of transferring digital or analogue signals as appropriate.

In operation, an operator can observe a sample located on stage 60 through eyepieces 62 in order to locate the sample as desired. The operator may also select the appropriate magnification by selecting between objective lenses 64. Alternatively, in an automated system, the microscope may be equipped with a motorized x-y stage to facilitate movement of the slide in relation to the microscope objective. Focus (z-axis) may also be controlled by the computer control system to avoid the need for operator intervention other than initially loading the sample. In operation, the computer system is would move the slide to a defined origin and then scan the slide in time-resolved fluorescence mode, halting to record the x-y coordinate of putative target fluorescence. The entire slide would be scanned in automated mode and the results recorded on the host computer. Optionally, the operator could be alerted to validate the identification of selected objects by requesting the control system to step to each recorded x-y position. In order to measure a fluorescence signal from the fluorescent probes in the sample, a pulsed signal is sent from FPGA 72 to drive 84, and another to sensor 58. The signal to drive 84 initiates a pulsed signal to pass to the LED, which then provides a pulsed UV excitation to the sample via objective lens 64. The pulsed signal to sensor 58 triggers sensor 58 to receive a fluorescence signal from the sample for a period commencing at a predetermined gate-delay after the end of a UV excitation pulse and ending before the commencement of the next UV excitation pulse. The signal to drive 84 also triggers controller 86 to trigger appropriate camera controls on sensor 58 to ensure that fluorescence data is acquired at the appropriate timing. The video output signal from sensor 58 is level shifted and amplified by analogue video processing circuit 78 and then submitted to a (8 to 16-bit) analogue to digital conversion in converter 80. The digital output is buffered in memory and processed by DSP unit 76 of FPGA module 72 to enhance signal to noise ratios using hardware coded convolution algorithms. The digital signal output from DSP unit 76 is connected to host PC 82 via a high speed serial link protocol such as USB 2.0 or FireWire (1394).

Results

Figure 3:
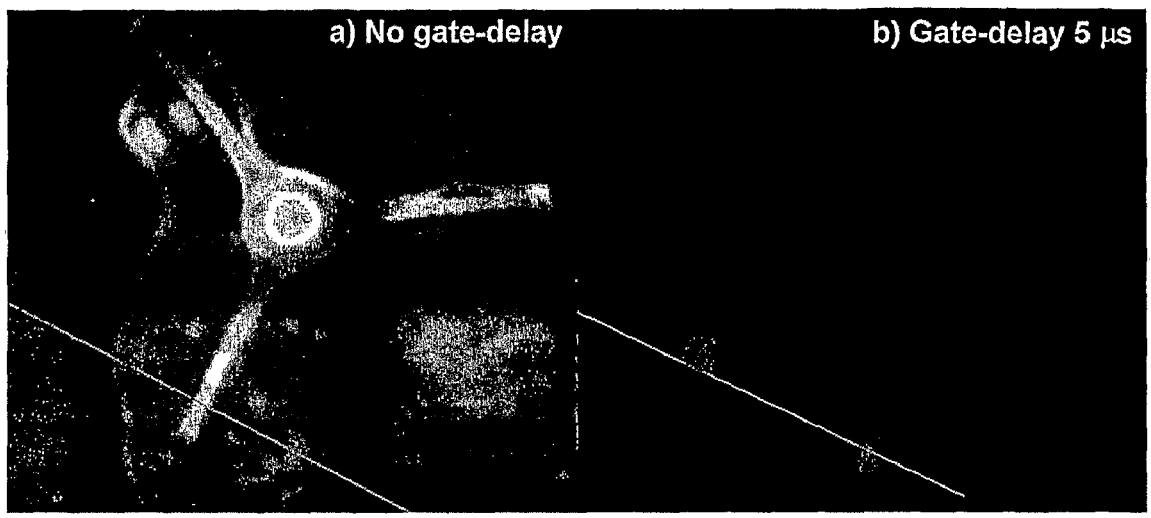
FIG. 3 shows fluorescence micrographs, wherein images A and B were captured with a UV LED excited TRFM using gate-delay periods of 0 µs and 5 µs respectively.
Figure 4:
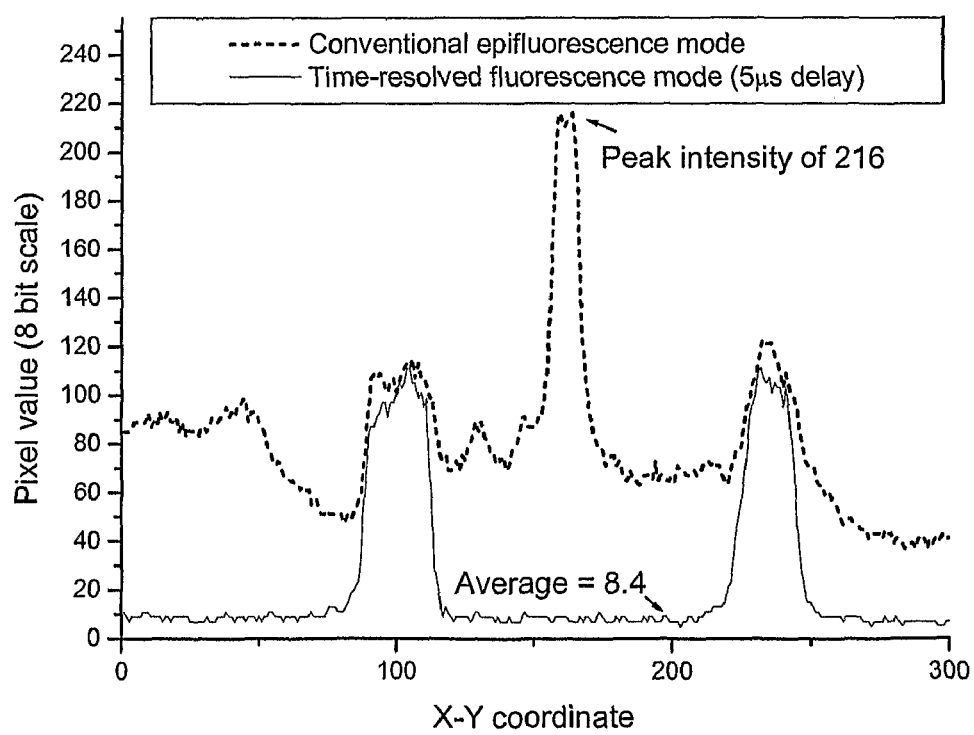
FIG. 4 shows graphs of pixel intensity as a function of position along a line transecting the two Giardia cysts shown in FIG. 3.

In image a) of FIG. 3, the fluorescence of the central desmid (Chlorophyta staurastrum; the trigonal organism) is strong by comparison with the immunofluorescently labelled Giardia cysts when viewed in conventional epifluorescence mode. Autofluorescence is greatly suppressed however when a short gate-delay of 5 µs is imposed and the two Giardia cysts are shown in image b) in stark relief against a dark background. The improvement in the signal to noise ratio (SNR) was determined by measuring the ratio of the fluorescent intensity of the cyst against (peak) autofluorescence intensity (pixel value on a scale from 0 to 255) in conventional epifluorescence mode and in TRFM mode. The ratio of signal intensity to autofluorescence in conventional epifluorescence mode was 123/216, resulting in a SNR of 0.57. A greatly improved SNR of 12.98 was achieved using time-resolved mode (109/8.4) so that the effective improvement in SNR was approximately 23-fold (15.98/0.57). The images shown in FIG. 3 were sampled as indicated by the white line to produce a line profile of intensity, shown in FIG. 4, that illustrates with improved clarity the reduction in autofluorescence that is achieved in TRFM mode. The SNR was calculated using the data reported from the line profile shown in FIG. 4, however if the peak intensity of the autofluorescence (measured at the desmid central ring; 252) is substituted into the equation, the improvement in the achieved SNR is 36-fold. A key advantage of the LED excitation over flashlamp based systems is the absence of any significant luminous output once the excitation pulse is extinguished. BHHST chelate has a typical fluorescence lifetime ($\tau$) of between 240 to 620 µs and is diminished by approximately 2% in the first instance and 0.8% in the second instance when a gate-delay of 5 µs is imposed. A significantly greater loss of fluorescence intensity occurs when the emission is captured after a gate-delay of 50 µs with losses of 18.8% and 7.7% respectively. The longer gate-delay is required for a flashlamp TRFM to permit decay of flashlamp plasma. Light from the flashlamp plasma is still present at significant levels for up to 100 µs following the main arc discharge and this causes further degradation of the SNR.

The invention claimed is:

1. A time resolved fluorescence detection system which does not have a shutter comprising:
    a pulsed light source for generating a light emission pulse to excite fluorescence in a fluorescently labeled species in a sample, the light emission pulse also capable of exciting autofluorescence in any autofluorophores present in the sample;
    an on-chip amplified charge coupled device (CCD) for detecting the fluorescence and outputting a florescence signal; and
    control circuitry to control the light source and the CCD, the control circuitry also being able to provide a pulsed signal to the light source to cause the light emission pulse, provide a gate delay between the light emission pulse and the commencement of detection by the CCD by maintaining the CCD in a non-operational condition during the gate delay, and to trigger the CCD at the end of the gate delay out of the non-operational condition to enable detection of the fluorescence during a detection period in which the fluorescence is distinguishable from the autofluorescence.

2. The fluorescence detection system of claim 1 wherein the non-operational condition of the CCD maintained by the control circuitry comprises the shunting to ground of a signal generated by the CCD during the gate delay.

3. The fluorescence detection system of claim 2 wherein the pulsed light source is a rapid decay light source.

4. The fluorescence detection system of claim 1, wherein the control circuitry is capable of enabling the CCD to detect the fluorescence in a single excitation cycle, the excitation cycle comprising a single light emission pulse, a single gate delay, and a single detection period.

5. The fluorescence detection system of claim 4 wherein the control circuitry is capable of enabling the CCD to output the fluorescence signal after the excitation cycle.

6. The fluorescence detection system of claim 1 wherein the CCD comprises a high gain on-chip amplified charge coupled device (CCD).

7. The fluorescence detection system of claim 2 further comprising a signal processing unit for processing the fluorescence signal.

8. The fluorescence detection system of claim 2, wherein the CCD is able to output the fluorescence signal as a time-resolved fluorescence image.

9. The fluorescence detection system of claim 8 further comprising external high speed memory for storing the time-resolved fluorescence image.

10. The fluorescence detection system of claim 2 wherein the CCD is able to output the fluorescence signal as a single time-resolved fluorescence image after a single excitation pulse.

11. The fluorescence detection system of claim 1 wherein the control circuitry is able to return the CCD to the non-operational condition at the end of the detection period.

12. The fluorescence detection system of claim 1 wherein the detection period is between about 10 and 800 microseconds long.

13. The fluorescence detection system of claim 1 or claim 2 wherein the control circuitry comprises a controller selected from the group of a printed circuit board, a computer, a microprocessor, a chip, a microchip or some other controller.

14. The fluorescence detection system of claim 1 or claim 2 wherein the pulsed light source is capable of generating successive light emission pulses, the duration of each of the emission pulses being between about 10 ns and about 200 microseconds, and the time between successive pulses being between about 1 microsecond and about 1 ms.

15. The fluorescence detection system of claim 1 or claim 2 wherein the control circuitry enables the CCD to detect the fluorescence in a plurality of excitation cycles, each excitation cycle comprising a light emission pulse, a gate delay period, and a detection period, wherein the fluorescence signal is outputted from the CCD after each excitation cycle.

16. The fluorescence detection system of claim 15 further comprising an integrator for off-chip integration of the outputted fluorescent signals.

17. The fluorescence detection system of claim 1 or claim 2 wherein the gate delay is less than about 10 microseconds.

18. The fluorescence detection system of claim 1 or claim 2 wherein, at the time after the emission pulse decay time, or of the autofluorescence, the ratio between the maximum intensity of the fluorescence and the maximum intensity of the autofluorescence is greater than about 1.5 to 1.

19. The fluorescence detection system of claim 1 or claim 2 wherein the time at which the fluorescence is distinguishable from the autofluorescence is less than about 10 microseconds.

20. The fluorescence detection system of claim 1 or claim 2 wherein the light source is capable of producing a light emission in the ultraviolet wavelength range.

21. The fluorescence detection system of claim 1 or claim 2 wherein the light source is an ultraviolet (UV) LED, and the system further includes a dichroic mirror disposed so as to direct UV light from the LED to the sample, the dichroic being highly reflective towards the frequency of the UV light emitted by the LED and highly transmissive towards the frequency of fluorescence emitted by the sample on excitation with the UV light emitted by the LED.

22. The fluorescence detection system of claim 1 wherein the fluorescence detection system comprises a microscope, and is a fluorescence detection microscope.

23. The fluorescence detection system of claim 1 or claim 2 wherein the light source is an LED light source with an optical output power of between about 2 and 400 mW.

24. The fluorescence detection system of claim 1 or claim 2 further including a beam homogenizer for avoidance of the formation of an intensity modulated pattern on the sample arising from the nature of the pulsed light source.

25. A method for detecting species in a sample, said species having been labelled with a fluorophore, said method comprising:
    placing the sample in a time resolved fluorescence detection system according claim 1;
    exposing the sample to a light pulse from the pulsed light source; and
    detecting fluorescence from the sample using the CCD in at least one excitation cycle comprising a single light emission pulse, a single gate delay, and a single detection period.

26. The method of claim 25 additionally comprising determining a number of fluorescent entities in the sample.

27. The method of claim 25 wherein the step of detecting comprises the steps of:
    waiting for a predetermined period after the end of a pulse from the light source, the predetermined period being substantially equal to the gate delay;
    detecting fluorescence during the detection period after the predetermined period; and
    stopping the detecting at the end of the detection period before commencement of a subsequent pulse from the light source.

28. The method of claim 27 wherein the fluorescence is detected in a single excitation cycle, the excitation cycle comprising a single light emission pulse, a single gate delay, and a single detection period.

29. The method of claim 28 wherein the CCD outputs the fluorescence signal after the excitation cycle.

30. The method of claim 27 wherein the predetermined period is less than about 10 microseconds.

31. The method of claim 25 also comprising magnifying the fluorescence from the sample before detecting it.

32. The method of claim 25 wherein the fluorescence is detected in a plurality of excitation cycles, the CCD outputs a fluorescence signal after each excitation cycle to provide a plurality of fluorescence signals, wherein the fluorescence signals are integrated.

33. A time resolved fluorescence detection system comprising:
    a pulsed light source for generating a light emission pulse to excite fluorescence in a sample, the light emission pulse also capable of exciting autofluorescence in any autofluorophores present in the sample; and
    an on-chip amplified charge coupled device (CCD) for detecting the fluorescence and outputting a fluorescence signal, wherein the light source and the CCD are controlled by control circuitry, the control circuitry also being able to provide a pulsed signal to the light source to cause the light emission pulse; provide a gate delay between the light emission pulse and the commencement of detection by the CCD by maintaining the CCD in a non-operational condition during the gate delay; and to trigger the CCD at the end of the gate delay out of the non-operational condition to enable detection of the fluorescence during a detection period in which the fluorescence is distinguishable from the autofluorescence.

34. The fluorescence detection system of claim 33 wherein the non-operational condition of the CCD maintained by the control circuitry comprises the shunting of a signal generated by the CCD during the gate delay to ground of a signal generated by the CCD during the gate delay.

35. The fluorescence detection system of claim 34 wherein the pulsed light source is a rapid decay light source.

36. The fluorescence detection system of claim 34 wherein the control circuitry enables the detector to detect the fluorescence in a single excitation cycle, the excitation cycle comprising a single light emission pulse, a single gate delay, and a single detection period.

37. The fluorescence detection system of claim 36 wherein the control circuitry enables the detector to output the fluorescence signal after the excitation cycle.

38. The fluorescence detection system of claim 33 wherein the detector is able to output the fluorescence signal as a single time-resolved fluorescence image after a single excitation pulse.

39. The fluorescence detection system of claim 33 wherein the CCD is capable of on-chip amplification of greater than 30.

40. The fluorescence detection system of claim 33 wherein the fluorescence detection system is a time resolved fluorescence detection system, a fluorescence detection microscope or a time resolved fluorescence detection microscope.

41. The fluorescence detection system of claim 33 also comprising an integrator for off-chip integration.

42. A time resolved fluorescence microscope comprising:
    a pulsed light source for generating a light emission pulse to excite fluorescence in a fluorescently labeled species in a sample, the light emission pulse also capable of exciting autofluorescence in any autofluorophores present in the sample;
    a dichroic mirror for directing the light emission from the light source towards the sample;
    an objective lens for magnifying the fluorescence from the sample;

a high gain on-chip amplified charge coupled device (CCD) for detecting the fluorescence from the sample and outputting a fluorescence signal;

an emission port for transmitting the fluorescence from the sample to the CCD; and control circuitry to: provide a pulsed signal to the light source to cause the light emission pulse; provide a gate delay of less than about 10 microseconds between the light pulse and the commencement of detection by the CCD by maintaining the CCD in a non-operational condition during the gate delay; and to trigger the CCD at the end of the gate delay out of the non-operational condition to enable detection of the fluorescence during a detection period in which the fluorescence is distinguishable from the autofluorescence.

43. The time resolved fluorescence microscope of claim 42 wherein the non-operational condition of the CCD maintained by the control circuitry comprises the shunting of a signal generated by the CCD during the gate delay to ground of a signal generated by the CCD during the gate delay.

44. The time resolved fluorescence microscope of claim 43 wherein the pulsed light source is a rapid decay light source.

45. The time resolved fluorescence microscope of claim 43 wherein the CCD is able to output a fluorescence signal as a time-resolved fluorescence image.

46. The time resolved fluorescence microscope of claim 45 further comprising external high speed memory for storing the time-resolved fluorescence image.

47. The time resolved fluorescence microscope of claim 43 wherein the detector is able to output the fluorescence signal as a single time-resolved fluorescence image after a single excitation pulse.

48. The time resolved fluorescence microscope of claim 42 wherein the control circuitry enables the detector to detect the fluorescence in a single excitation cycle, the excitation cycle comprising a single light emission pulse, a single gate delay, and a single detection period.

49. The time resolved fluorescence microscope of claim 48 wherein the control circuitry enables the detector to output the fluorescence signal after the excitation cycle.

50. A kit for modifying a fluorescence microscope to provide a time resolved fluorescence microscope which does not have a shutter; the kit comprising:

a pulsed light source for generating a light emission pulse to excite fluorescence in a fluorescently labeled species in a sample, the light emission pulse also capable of exciting autofluorescence in any autofluorophores present in the sample; and a high gain on-chip amplified charge coupled device (CCD) for detecting the fluorescence from the sample;

control circuitry to control the light source and the CCD, the control circuitry also being able to: provide a pulsed signal to the light source to cause the light emission pulse; provide a gate delay between the light emission pulse and the commencement of detection by the CCD by maintaining the CCD in a non-operational condition during the gate delay; and to trigger the CCD at the end of the gate delay out of the non-operational condition to enable detection of the fluorescence during a detection period in which the fluorescence is distinguishable from the autofluorescence.

51. The kit of claim 50 wherein the non-operational condition of the CCD maintained by the control circuitry comprises the shunting of a signal generated by the CCD during the gate delay to ground of a signal generated by the CCD during the gate delay.

52. The kit of claim 50 wherein the pulsed light source is a rapid decay light source.

53. The kit of claim 50 wherein the control circuitry comprises a controller selected from the group of a printed circuit board, a computer, a microprocessor, a chip, a microchip or some other controller.

54. The kit of claim 50 additionally comprising one or more of:

a collimator;

a dichroic mirror, which is reflective, partially reflective or highly reflective towards the light emission from the light source, and its transmissive, partially transmissive or highly transmissive towards the fluorescence;

a first light transmitter for transmitting the light emission towards a sample;

a second light transmitter for transmitting the fluorescence towards a detector and/or an eyepiece; and a housing, for housing any one or more of the above.

55. A method for modifying a fluorescence microscope to provide a time resolved fluorescence microscope which does not have a shutter, the method comprising fitting to said microscope:

a pulsed light source for generating a light emission to excite fluorescence in a fluorescently labeled species in a sample, the light emission pulse also capable of exciting autofluorescence in any autofluorophores present in the sample; and a high gain on-chip amplified charge coupled device (CCD) for detecting the fluorescence from the sample;

control circuitry to control the light source and the CCD, the control circuitry also being able to: provide a pulsed signal to the light source to cause the light emission pulse; provide a gate delay between the light emission pulse and the commencement of detection by the CCD by maintaining the CCD in a non-operational condition during the gate delay; and to trigger the CCD at the end of the gate delay out of the non-operational condition to enable detection of the fluorescence during a detection period in which the fluorescence is distinguishable from the autofluorescence.

56. The method of claim 55 wherein the non-operational condition of the CCD maintained by the control circuitry comprises the shunting of a signal generated by the CCD during the gate delay to ground of a signal generated by the CCD during the gate delay.

57. The method of claim 56 wherein the pulsed light source is a rapid decay light source.

58. The method of claim 56 wherein the control circuitry is capable of enabling the CCD to detect the fluorescence in a single excitation cycle, the excitation cycle comprising a single light emission pulse, a single gate delay, and a single detection period.

59. The fluorescence detection system of claim 56 wherein the CCD is able to output the fluorescence signal as a single time-resolved fluorescence image after a single excitation pulse.

60. The method of claim 55 wherein the control circuitry comprises a controller selected from the group of a printed circuit board, a computer, a microprocessor, a chip, a microchip or some other controller.

61. The method of claim 55 additionally comprising fitting to the microscope one or more of:

a collimator;

a dichroic mirror, which is reflective, partially reflective or highly reflective towards the light emission, and is transmissive, partially transmissive or highly transmissive towards the fluorescence;

a first light transmitter for transmitting the light emission towards a sample;

a second light transmitter for transmitting the fluorescence towards the CCD and/or an eyepiece; and a housing, for housing any one or more of the above.

62. A fluorescence microscope modified according to the method of claim 55.

63. A method for detecting a species in a sample, said species having been labeled with a fluorophore, said method comprising:
   a) providing a pulsed light source for generating a light emission pulse;
   b) providing a on-chip amplified charge coupled device (CCD) having a high gain;
   c) providing control circuitry for controlling the light source and the detector;
   d) providing a pulsed signal from the control circuitry to the light source to generate the light emission pulse;
   e) exposing the sample to the light emission pulse to excite fluorescence in the fluorophore;
   f) waiting for a predetermined time, during which time the control circuitry maintains the CCD in a non-operational condition such that autofluorescence excited by the excitation pulse in any autofluorophores present in the sample is not detected;
   g) after the predetermined time has elapsed triggering the CCD out of the non-operational state using the control circuitry to switch the detector into an operational condition to detect the fluorescence during a predetermined detection period in which the fluorescence is distinguishable from the autofluorescence, thereby to generate a fluorescence signal;
   h) after the predetermined detection period, returning the CCD to the non-operational condition using the control circuitry; and
   i) outputting the fluorescence signal from the CCD.

64. The fluorescence detection system of claim 63 wherein the non-operational condition of the CCD maintained by the control circuitry comprises the shunting of a signal generated by the CCD during the gate delay to ground of a signal generated by the CCD during the gate delay.

65. The method of claim 64 wherein step a) comprises providing a rapid decay pulsed light source for generating a light emission pulse with a rapid decay profile.

66. The method of claim 64 wherein the fluorescence signal of step (g) comprises a time-resolved fluorescence image, and step (i) comprises outputting the time-resolved fluorescence image from the detector and storing the image in external high speed memory.

67. The method of claim 63 wherein in step (i) the fluorescence signal is output to a signal processing unit.

68. The method of claim 63 comprising repeating steps c) to g) to generate and output a plurality of fluorescence signals to an off-chip integrator, thereby to integrate the detected fluorescence.

* * * * *